US008383360B2

(12) United States Patent
Van de Water et al.

(10) Patent No.: US 8,383,360 B2
(45) Date of Patent: Feb. 26, 2013

(54) METHODS OF DIAGNOSING AND TREATING AUTISM

(75) Inventors: Judy Van de Water, Capay, CA (US); Daniel Braunschweig, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/855,558

(22) Filed: Aug. 12, 2010

(65) Prior Publication Data

US 2011/0038872 A1 Feb. 17, 2011

Related U.S. Application Data

(60) Provisional application No. 61/234,110, filed on Aug. 14, 2009.

(51) Int. Cl.
  *G01N 33/53* (2006.01)
  *G01N 33/542* (2006.01)
  *G01N 33/568* (2006.01)
(52) U.S. Cl. ...... 435/7.92; 435/7.9; 435/7.93; 435/7.95; 436/501; 436/503; 436/504
(58) Field of Classification Search .................. None
See application file for complete search history.

(56) References Cited

U.S. PATENT DOCUMENTS

| 7,452,681 B2 | 11/2008 | Amaral et al. |
| 8,043,820 B2 | 10/2011 | Amaral et al. |

FOREIGN PATENT DOCUMENTS

| WO | WO 2005/007090 | 1/2005 |
| WO | WO 2006/121912 A2 | 11/2006 |
| WO | WO 2006/121952 A2 | 11/2006 |

OTHER PUBLICATIONS

Chauhan et al, 2008, J. Neurochem, 106(1), p. 44.*
Becker et al., 1989, Clin. Chem., 35(1)), pp. 2190-2195.*
Ashwood et al., "A review of autism and the immune response," Clinical and Developmental Immunology, vol. 11(2), pp. 165-174 (Jun. 2004).
Ashwood et al., "Is autism an autoimmune disease?" Autoimmune Rev., vol. 3(7-8), 13 pgs. (Nov. 2004).
Bauman et al., "The development of mother-infant interactions after neonatal amygdale lesions in rhesus monkeys," The Journal of Neuroscience, vol. 24(3), pp. 711-721 (Jan. 21, 2004).
Bauman et al., "The development of social behavior following neonatal amygdale lesions in rhesus monkeys," Journal of Cognitive Neuroscience, vol. 16(8), pp. 1388-1411 (2004).
Braunschweig et al "Autism: Maternally derived antibodies specific for fetal brain proteins," Neurotoxicology, Tox Press, vol. 9, No. 2, Nov. 2007, pp. 226-231.
Cabanlit et al., "Brain-specific Autoantibodies in the Plasma of Subjects with Autistic Spectrum Disorder," Ann. N.Y. Acad. Sci., vol. 1107, pp. 92-103 (2007).
Connolly et al., "Serum autoantibodies to brain in Landau-Kleffner variant, autism, and other neurologic disorders," The Journal of Pediatrics, vol. 134(5), pp. 607-613 (May 1999).
Cook et al., "Receptor inhibition by immunoglobulins: Specific inhibition by autistic children, their relatives, and control subjects," Journal of Autism and Developmental Disorders, vol. 23(1), pp. 67-78 (1993).
Croen et al., "Maternal autoimmune diseases, asthma and allergies, and childhood autism spectrum disorders," Arch. Pediatr. Adolesc. Med., vol. 159, pp. 151-157 (Feb. 2005).
Dalton et al., "Maternal neuronal antibodies associated with autism and a language disorder," Annals of Neurology, vol. 53(4), pp. 533-537 (Apr. 2003).
Eigsti et al., "A systems neuroscience approach to autism: Biological, cognitive and clinical perspectives," Mental Retardation and Developmental Disabilities, Research Reviews, vol. 9, pp. 206-216 (2003).
Emery et al., "The effects of bilateral lesions of the amygdala on dyadic social interactions in rhesus monkeys (*Macaca mulatta*)," Behavioral Neuroscience, vol. 115(3), pp. 515-544 (2001).
Flannery et al., "A test of the immunoreactive theory for the origin of neurodevelopmental disorders in the offspring of women with immune disorder," Cortex, vol. 30, pp. 635-646 (1994).
Gothard et al., "How do rhesus monkeys (*Macaca mulatta*) scan faces in a visual paired comparison task?" Anim. Cogn., vol. 7, pp. 25-36 (2004).
Kiessling et al., "Antineuronal antibodies: Tics and obsessive-compulsive symptoms," Developmental and Behavioral Pediatrics, vol. 15(6), pp. 421-425 (Dec. 1994).
Plioplys et al., "Anti-CNS antibodies in childhood neurologic diseases," Neuropediatrics, vol. 20, pp. 93-102 (1989).
Plioplys et al., "Lymphocyte function in autism and rett syndrome," Neuropsychobiology, vol. 29, pp. 12-16 (1994).
Prather et al., "Letter to Neuroscience: Increased social fear and decreased fear of objects in monkeys with neonatal amygdale lesions," Neuroscience, vol. 106(4), pp. 653-658 (2001).

(Continued)

*Primary Examiner* — Olga N Chernyshev
(74) *Attorney, Agent, or Firm* — Kilpatrick Townsend & Stockton LLP

(57) ABSTRACT

The present invention provides diagnostic methods for determining the risk of developing an autism spectrum disorder (ASD) in a fetus or child by detecting in a biological sample from the mother antibodies that bind to one or more biomarkers selected from the group consisting of lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR). The invention further provides methods of preventing or reducing the risk of a fetus or child developing an ASD by administering to the mother an agent that blocks the binding of maternal antibodies to the one or more fetal biomarkers listed above or by removing from the mother antibodies that bind to the one or more fetal biomarkers.

20 Claims, 11 Drawing Sheets

OTHER PUBLICATIONS

Sankar "Studies on blood platelets, blood enzymes, and leucocyte chromosome breakage in childhood schizophrenia," Behavioral Neuropsychiatry, vol. 2, No. 11, Feb. 1971, pp. 2-10.

Schorer "Muscular dystrophy and the mind," Psychosomatic Medicine, vol. 26, Jan. 1964, pp. 5-13.

Shamy et al., Hippocampal volume is preserved and fails to predict recognition memory impairment in aged rhesus monkeys (*Macaca mulatto*), Neurobiology of Aging, 11 pgs. (2005).

Silva et al., "Autoantibody repertoires to brain tissue in autism nuclear families," Journal of Neuroimmunology, vol. 152, pp. 176-182 (2004).

Singer et al "Prenatal exposure to antibodies from mothers of children with autism produces neurobehavioral alterations: a pregnant dam mouse model," Journal of Neuroimmunology, vol. 211, No. 1-2, Jun. 2009, pp. 39-48.

Singer et al "Antibodies against fetal brain insera of mothers with autistic children," Journal of Neuroimmunology, vol. 194, No. 1-2, Feb. 2008, pp. 165-172.

Singh et al., "Immunodiagnosis and immunotherapy in autistic children," Ann. NY Acad. Sci., vol. 540, pp. 602-604 (1994).

Singh et al., "Antibodies to myelin basic protein in children with autistic behavior," Brain, Behavior, and Immunity, vol. 7, pp. 97-103 (1993).

Singh et al., "Circulating autoantibodies to neuronal and glial filament proteins in autism," Pediatric Neurology, vol. 17(1), pp. 88-90 (1997).

Singh et al., "Prevalence of serum antibodies to caudate nucleus in autistic children," Neuroscience Letters, vol. 355, pp. 53-56 (2004).

Sparks et al., "Brain structural abnormalities in young children with autism spectrum disorder," Neurology, vol. 59, pp. 184-192 (Jul. 2002).

Todd et al., "Demonstration of inter- and intraspecies differences in serotonin binding sites by antibodies from an autistic child," PNAS, vol. 82, pp. 612-616 (Jan. 1985).

Vargas et al., "Neuroglial activation and neuroinflammation in the brain of patients with autism," Ann. Neurol., vol. 57, pp. 67-81 (2005).

Warren et al., "Detection of maternal antibodies in infantile autism," J. Am. Acad. Child Adolesc. Psychiatry, vol. 29(6), pp. 873-877 (Nov. 1990).

Weizman et al., "Abnormal immune response to brain tissue antigen in the syndrome of autism," Am. J. Psychiatry, vol. 139(11), pp. 1462-1465 (Nov. 1982).

Willis et al., "Autoantibodies in Autism Spectrum Disorders (ASD)," Ann. N.Y. Acad. Sci. 1107, pp. 79-91 (2007).

Willis et al., "Detection of Autoantibodies to Neural Cells of the Cerebellum in the Plasma of Subjects with Autism Spectrum Disorders," Brain Behav Immun., vol. 23, No. 1, pp. 64-74 (2009).

International Search Report, PCT Application No. PCT/US2010/045343, International filed Aug. 12, 2010, Dated Dec. 30, 2010, 6 pages.

Azad et al., "Comparative Detection of Measles Specific IGM Antibody in Serum and Saliva by an Antibody-Capture IGM Enzyme Immunoassay (EIA)," Iranian Journal of Allergy, Asthma and Immunology, 2003, vol. 2, No. 3, pp. 149-154.

Litt et al., "Detection of anti-pertussis toxin IgG in oral fluids for use in diagnosis and surveillance of *Bordetella pertussis* infection in children and young adults," Journal of Medical Microbiology, 2006, vol. 55, pp. 1223-1228.

Luzza et al., "Salivary Immunoglobulin G Assay to Diagnose *Helicobacter pylori* Infection in Children," Journal of Clinical Microbiology, 1997, vol. 35, No. 12, pp. 3358-3360.

Thongcharoen et al., "Immunoglobulin G Antibody Capture Enzyme-Linked Immunosorbent Assay: a Versatile Assay for Detection of Anti-Human Immunodeficiency Virus Type 1 and 2 Antibodies in Body Fluids," Journal of Clinical Microbiology, 1992, vol. 30, No. 12, pp. 3288-3289.

* cited by examiner

METHODS OF DIAGNOSING AND TREATING AUTISM

CROSS-REFERENCE TO RELATED APPLICATIONS

This application claims the benefit of U.S. Provisional Application No. 61/234,110, filed on Aug. 14, 2009, the entire contents of which are hereby incorporated herein by reference for all purposes.

STATEMENT AS TO RIGHTS TO INVENTIONS MADE UNDER FEDERALLY SPONSORED RESEARCH AND DEVELOPMENT

This invention was made with government support under Grant 1-P01-ES11269-01, awarded by the NIEHS and Grant R829388, awarded by the EPA. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -1998-1.txt, created on Jun. 7, 2012, 4,096 bytes, machine format IBM-PC, MS-Windows operating system, is hereby incorporated by reference in its entirety for all purposes.

FIELD OF THE INVENTION

The present invention relates to the diagnosis and prevention or inhibition of an autism spectrum disorder in a fetus.

BACKGROUND OF THE INVENTION

Autism spectrum disorders (ASD) are a group of heterogeneous neurodevelopmental disorders manifesting in childhood and defined by deficits in communication and reciprocal social interaction and often accompanied by stereotypical behaviors (American Psychiatric Association, *Diagnostic and Statistical Manual of Mental Disorders*, Fourth Edition ("DSM-IV") 2000, Washington, D.C.). Although strong genetic links have been demonstrated in numerous reports (reviewed in Ashwood et al., *J Leukoc Biol*. (2006) 80(1):1-15), a clear etiologic basis for ASD is lacking A role for immune system involvement in ASD development has been supported in a steadily increasing body of literature (Ashwood, supra; Enstrom et al., *Curr Opin Investig Drugs*. (2009) 10(5):463-73; and Li, et al., *J Neuroimmunol*. (2009) 207(1-2):111-6). Findings of abnormal immune responses, neuroinflammation and microglial activation, and the presence of maternal autoantibodies to rodent and human fetal brain tissue have been described (Vargas et al., *Ann Neurol*. (2005) 57(1):67-81; and Singer et al., *J Neuroimmunol*. (2009) 211(1-2):39-48.

We previously described significant associations between reactivity of plasma antibodies to human fetal brain tissue among mothers of children with an ASD. See, U.S. Pat. No. 7,452,681. In a case control cohort of mothers of ASD children, mothers of typically developing children and mothers of non-ASD developmentally delayed (DD) children, a significant association between IgG immunoreactivity to protein bands at 37 kD and 73 kD was demonstrated. Furthermore, an odds ration of 5.69 was observed for the band at 37 kD alone. See, Braunschweig et al., *Neurotoxicology*. (2008) 29(2):226-31.

Abnormalities in the maternal immune milieu during pregnancy have been implicated in ASD in several studies. Facilitated passage of IgG antibodies is a well established phenomenon thought to generally provide protection for the newborn child (Simister et al., *Vaccine*. (2003) 21(24):3365-9). However, together with IgG antibodies that are immunoprotective, autoantibodies that react to fetal 'self'-proteins can also cross the placenta. A recent report demonstrated maternal IgG antibody reactivity to rodent Purkinje cells in a mother of multiple children with ASD, as well as the presence of behavioral deficits in pups of a mouse injected during gestation with her serum (Dalton et al., *Ann Neurol*. (2003) 53(4):533-7). In another study, mothers of children with autism and their affected children were found to have consistent patterns of antibody reactivity against rat pre-natal (day 18) brain proteins. In contrast, unaffected children and control mothers had alternative patterns of reactivity (Zimmerman et al., *Brain Behav Immun*. (2007) 21(3):351-7).

The preponderance of evidence suggests a pre-natal or early post-natal etiology for autism, potentially involving errant developmental cues. Advances in understanding the role of immune system components during fetal neurodevelopment combined with the cross-talk between the maternal and fetal immune systems, led us to investigate the profiles of autoantibody reactivity in mothers of children with autism and to compare them with profiles from mothers of typically developing children and from mothers of children with other developmental disorders excluding autism.

BRIEF SUMMARY OF THE INVENTION

In one aspect, the present invention provides methods of determining a risk to an offspring, e.g., fetus or child, of developing an autism spectrum disorder (ASD). In a related aspect, the present invention provides methods of determining a risk that a mother or potential mother will bear a child who will develop an autism spectrum disorder (ASD). In some embodiments, the methods comprise identifying in a biological sample from the mother of the offspring the presence of maternal antibodies that bind to 1, 2, 3, 4, 5, 6, 7, 8, 9, 10, 11, 12, 13, or more, biomarkers selected from the group consisting of lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR), wherein the presence of maternal antibodies that bind to the one or more biomarkers indicates an increased risk of the offspring for developing an ASD.

In some embodiments, the presence of maternal antibodies that bind to one, two, three or all biomarkers selected from lactate dehydrogenase (LDH), guanine deaminase (GDA), collapsin response mediator protein 1 (CRMP1) and stress-induced phosphoprotein 1 (STIP1) is determined. In some embodiments, the presence of maternal antibodies that bind to one, two or all biomarkers selected from lactate dehydrogenase (LDH), collapsin response mediator protein 1 (CRMP1) and stress-induced phosphoprotein 1 (STIP1) is determined. In some embodiments, the presence of maternal antibodies that bind to one, two or all biomarkers selected from guanine deaminase (GDA), collapsin response mediator protein 1 (CRMP1) and stress-induced phosphoprotein 1 (STIP1) is determined. In some embodiments, the presence of maternal antibodies that bind to one or both lactate dehydrogenase (LDH) and collapsin response mediator protein 1 (CRMP1) is determined. In some embodiments, the presence of maternal antibodies that bind to one or both guanine deaminase (GDA) and collapsin response mediator protein 1 (CRMP1) is determined. In some embodiments, the presence of maternal antibodies that bind to one or both lactate dehydrogenase (LDH) and stress-induced phosphoprotein 1 (STIP1) is determined. In some embodiments, the presence of maternal antibodies that bind to one or both guanine deaminase (GDA) and stress-induced phosphoprotein 1 (STIP1) is determined. In some embodiments, the presence of maternal antibodies that bind to lactate dehydrogenase (LDH) is determined. In some embodiments, the presence of maternal antibodies that bind to guanine deaminase (GDA) is determined. In some embodiments, the presence of maternal antibodies that bind to collapsin response mediator protein 1 (CRMP1) is determined. In some embodiments, the presence of maternal antibodies that bind to stress-induced phosphoprotein 1 (STIP1) is determined.

In some embodiments, the presence of maternal antibodies that bind to one, two, three or all biomarkers selected from lactate dehydrogenase (LDH), guanine deaminase (GDA), dihydropyrimidinase-like protein 2 (DPYSL2) and stress-induced phosphoprotein 1 (STIP1) is determined. In some embodiments, the presence of maternal antibodies that bind to one, two or all biomarkers selected from lactate dehydrogenase (LDH), dihydropyrimidinase-like protein 2 (DPYSL2) and stress-induced phosphoprotein 1 (STIP1) is determined. In some embodiments, the presence of maternal antibodies that bind to one, two or all biomarkers selected from guanine deaminase (GDA), dihydropyrimidinase-like protein 2 (DPYSL2) and stress-induced phosphoprotein 1 (STIP1) is determined. In some embodiments, the presence of maternal antibodies that bind to one or both lactate dehydrogenase (LDH) and dihydropyrimidinase-like protein 2 (DPYSL2) is determined. In some embodiments, the presence of maternal antibodies that bind to one or both guanine deaminase (GDA) and dihydropyrimidinase-like protein 2 (DPYSL2) is determined. In some embodiments, the presence of maternal antibodies that bind to dihydropyrimidinase-like protein 2 (DPYSL2) is determined.

In a further aspect, the invention provides methods of determining a risk to an offspring, e.g., fetus or child, of developing an autism spectrum disorder (ASD) or determining a risk that a mother or potential mother will bear a child who will develop an autism spectrum disorder (ASD) by identifying in a biological sample from the mother of the offspring the presence of maternal antibodies that bind to one or more proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase, wherein the presence of maternal antibodies that bind to the one or more proteins indicates an increased risk of the offspring for developing an ASD. The determination of the presence of maternal antibodies against one or more proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase can be performed in conjunction with or independently from the determination of maternal antibodies against the one or more biomarkers described herein.

In some embodiments, the diagnostic methods comprise the step of contacting the biological sample from the patient with one or more polypeptides of one or more biomarkers selected from the group consisting of lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR), or antigenic fragments thereof, or mimeotopes thereof. The polypeptide, antigenic fragment thereof, or mimeotope thereof from the one or more biomarkers can be attached to a solid support, including without limitation, a multiwell plate, an ELISA plate, a microarray chip, a bead, a porous strip, a nitrocellulose membrane.

In some embodiments, the biological sample from the mother or potential mother is contacted with a polypeptide or antigenic fragment thereof or a mimeotope of one, two, three or all biomarkers selected from lactate dehydrogenase (LDH), guanine deaminase (GDA), collapsin response mediator protein 1 (CRMP1) and stress-induced phosphoprotein 1 (STIP1). In some embodiments, the biological sample from the mother or potential mother is contacted with a polypeptide or antigenic fragment thereof or a mimeotope of one, two or all biomarkers selected from lactate dehydrogenase (LDH), collapsin response mediator protein 1 (CRMP1) and stress-induced phosphoprotein 1 (STIP1). In some embodiments, the biological sample from the mother or potential mother is contacted with a polypeptide or antigenic fragment thereof or a mimeotope of one, two or all biomarkers selected from guanine deaminase (GDA), collapsin response mediator protein 1 (CRMP1) and stress-induced phosphoprotein 1 (STIP1). In some embodiments, the biological sample from the mother or potential mother is contacted with a polypeptide or antigenic fragment thereof or a mimeotope of one or both of lactate dehydrogenase (LDH) and collapsin response mediator protein 1 (CRMP1). In some embodiments, the biological sample from the mother or potential mother is contacted with a polypeptide or antigenic fragment thereof or a mimeotope of one or both of guanine deaminase (GDA) and collapsin response mediator protein 1 (CRMP1). In some embodiments, the biological sample from the mother or potential mother is contacted with a polypeptide or antigenic fragment thereof or a mimeotope of one or both of lactate dehydrogenase (LDH) and stress-induced phosphoprotein 1 (STIP1). In some embodiments, the biological sample from the mother or potential mother is contacted with a polypeptide or antigenic fragment thereof or a mimeotope of one or both of guanine deaminase (GDA) and stress-induced phosphoprotein 1 (STIP1). In some embodiments, the biological sample from the mother or potential mother is contacted with a polypeptide or antigenic fragment thereof or a mimeotope of lactate dehydrogenase (LDH). In some embodiments, the biological sample from the mother or potential mother is contacted with a polypeptide or antigenic fragment thereof or a mimeotope of guanine deaminase (GDA). In some embodiments, the biological sample from the mother or potential mother is contacted with a polypeptide or antigenic fragment thereof or a mimeotope of collapsin response mediator protein 1 (CRMP1). In some embodiments, the biological sample from the mother or potential mother is contacted with a polypeptide or antigenic fragment thereof or a mimeotope of stress-induced phosphoprotein 1 (STIP1).

In some embodiments, the biological sample from the mother or potential mother is contacted with a polypeptide or antigenic fragment thereof or a mimeotope of one, two, three or all biomarkers selected from lactate dehydrogenase (LDH), guanine deaminase (GDA), dihydropyrimidinase-like protein 2 (DPYSL2) and stress-induced phosphoprotein 1 (STIP1). In some embodiments, the biological sample from the mother or potential mother is contacted with a polypeptide or antigenic fragment thereof or a mimeotope of one, two or all biomarkers selected from lactate dehydrogenase (LDH), dihydropyrimidinase-like protein 2 (DPYSL2) and stress-induced phosphoprotein 1 (STIP1). In some embodiments, the biological sample from the mother or potential mother is contacted with a polypeptide or antigenic fragment thereof or a mimeotope of one, two or all biomarkers selected from guanine deaminase (GDA), dihydropyrimidinase-like protein 2 (DPYSL2) and stress-induced phosphoprotein 1 (STIP1). In some embodiments, the biological sample from the mother or potential mother is contacted with a polypeptide or antigenic fragment thereof or a mimeotope of one or both of lactate dehydrogenase (LDH) and dihydropyrimidinase-like protein 2 (DPYSL2). In some embodiments, the biological sample from the mother or potential mother is contacted with a polypeptide or antigenic fragment thereof or a mimeotope of one or both of guanine deaminase (GDA) and dihydropyrimidinase-like protein 2 (DPYSL2). In some embodiments, the biological sample from the mother or potential mother is contacted with a polypeptide or antigenic fragment thereof or a mimeotope of dihydropyrimidinase-like protein 2 (DPYSL2).

In some embodiments, the lactate dehydrogenase is the LDH-A subunit, i.e., encoded by the human gene LDHA. In some embodiments, the lactate dehydrogenase is the LDH-B subunit, i.e., encoded by the human gene LDHB. In some embodiments, the lactate dehydrogenase is both the LDH-A and LDH-B subunits. In some embodiments, the lactate dehydrogenase is a tetramer composed of four LDH-A subunits or four LDH-B subunits. In some embodiments, lactate dehydrogenase is a tetramer composed of combinations of LDH-A and LDH-B subunits. In some embodiments, the LDH is human LDH.

In some embodiments, the offspring is a neonate (i.e., a newborn up to four weeks old). In some embodiments, the offspring is a fetus. In some embodiments, the fetus is gestating in the mother. The biological sample can be taken from the mother anytime during pregnancy. In some embodiments, the biological sample is taken after the fetal brain has begun to develop, e.g., after about the $12^{th}$ week of gestation. In some embodiments, the biological sample is taken during the second trimester of pregnancy. In some embodiments, the biological sample is taken during the third trimester of pregnancy.

In some embodiments, the fetus is not yet conceived. The biological sample can be taken from any woman of childbearing age, before or after conception of the fetus, or after the birth of the child.

In some embodiments, the methods further comprise the step of obtaining the biological sample from the mother. In some embodiments, the biological sample from the mother is selected from the group consisting of blood, serum, plasma, amniotic fluid, milk and saliva.

In some embodiments, the mother has a child with an ASD. In some embodiments, the mother has a familial history of ASD. In some embodiments, the mother has a familial history of autoimmune disease.

In some embodiments, the mother is a human.

In some embodiments, the antibodies that bind to one or more biomarkers described herein or a fragment thereof are detected, e.g., by Western blot, dot blot, enzyme-linked immunosorbant assay ("ELISA"), radioimmunoassay ("RIA"), immunoprecipitation, electrochemiluminescence, microarray, or a multiplex bead-based assay (e.g., a Luminex-bead or a fluorescent-bead assay).

In a further aspect, the invention provides methods of preventing or reducing the risk of a fetus developing an ASD comprising administering to the mother of the fetus an agent that blocks the binding of maternal antibodies to one or more fetal biomarkers selected from the group consisting of lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR), whereby blocking the binding to the one or more fetal biomarkers by the maternal antibodies prevents or reduces the risk of the fetus developing an ASD.

In some embodiments, an agent that blocks the binding of maternal antibodies to one, two, three or all biomarkers selected from lactate dehydrogenase (LDH), guanine deaminase (GDA), collapsin response mediator protein 1 (CRMP1) and stress-induced phosphoprotein 1 (STIP1) is administered. In some embodiments, an agent that blocks the binding of maternal antibodies to one, two or all biomarkers selected from lactate dehydrogenase (LDH), collapsin response mediator protein 1 (CRMP1) and stress-induced phosphoprotein 1 (STIP1) is administered. In some embodiments, an agent that blocks the binding of maternal antibodies to one, two or all biomarkers selected from guanine deaminase (GDA), collapsin response mediator protein 1 (CRMP1) and stress-induced phosphoprotein 1 (STIP1) is administered. In some embodiments, an agent that blocks the binding of maternal antibodies to one or both of lactate dehydrogenase (LDH) and collapsin response mediator protein 1 (CRMP1) is administered. In some embodiments, an agent that blocks the binding of maternal antibodies to one or both of guanine deaminase (GDA) and collapsin response mediator protein 1 (CRMP1) is administered. In some embodiments, an agent that blocks the binding of maternal antibodies to one or both of lactate dehydrogenase (LDH) and stress-induced phosphoprotein 1 (STIP1) is administered. In some embodiments, an agent that blocks the binding of maternal antibodies to one or both of guanine deaminase (GDA) and stress-induced phosphoprotein 1 (STIP1) is administered. In some embodiments, an agent that blocks the binding of maternal antibodies to lactate dehydrogenase (LDH) is administered. In some embodiments, an agent that blocks the binding of maternal antibodies to guanine deaminase (GDA) is administered. In some embodiments, an agent that blocks the binding of maternal antibodies to collapsin response mediator protein 1 (CRMP1) is administered. In some embodiments, an agent that blocks the binding of maternal antibodies to stress-induced phosphoprotein 1 (STIP1) is administered.

In some embodiments, an agent that blocks the binding of maternal antibodies to one, two, three or all biomarkers selected from lactate dehydrogenase (LDH), guanine deaminase (GDA), dihydropyrimidinase-like protein 2 (DPYSL2) and stress-induced phosphoprotein 1 (STIP1) is administered. In some embodiments, an agent that blocks the binding of maternal antibodies to one, two or all biomarkers selected from lactate dehydrogenase (LDH), dihydropyrimidinase-like protein 2 (DPYSL2) and stress-induced phosphoprotein 1 (STIP1) is administered. In some embodiments, an agent that blocks the binding of maternal antibodies to one, two or all biomarkers selected from guanine deaminase (GDA), dihydropyrimidinase-like protein 2 (DPYSL2) and stress-induced phosphoprotein 1 (STIP1) is administered. In some embodiments, an agent that blocks the binding of maternal antibodies to one or both of lactate dehydrogenase (LDH) and dihydropyrimidinase-like protein 2 (DPYSL2) is administered. In some embodiments, an agent that blocks the binding of maternal antibodies to one or both of guanine deaminase (GDA) and dihydropyrimidinase-like protein 2 (DPYSL2) is administered. In some embodiments, an agent that blocks the binding of maternal antibodies to dihydropyrimidinase-like protein 2 (DPYSL2) is administered.

In some embodiments, the agent is a polypeptide of the biomarker or an antigenic fragment thereof. In some embodiments, the agent is a mimeotope of a polypeptide of the biomarker.

In some embodiments, the maternal antibodies bind at least one of LDH-A and LDH-B, e.g., either as subunits or as tetramers.

In a further aspect, the invention provides methods of preventing or reducing the risk of a fetus developing an ASD comprising administering to the mother of the fetus an agent that blocks the binding of maternal antibodies to one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase, whereby blocking the binding to the one or more fetal proteins of the maternal antibodies prevents or reduces the risk of the fetus developing an ASD. The blocking of the binding of maternal antibodies against one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase can be performed in conjunction with or independently from the blocking of the binding of maternal antibodies against the one or more biomarkers described herein.

In some embodiments, the agent is administered intravenously. In some embodiments, the agent is administered orally.

The blocking agent can be administered to the mother anytime during pregnancy. In some embodiments, the blocking agent is administered after the fetal brain has begun to develop, e.g., after about the $12^{th}$ week of gestation. In some embodiments, the blocking agent is administered during the second trimester of pregnancy. In some embodiments, the blocking agent is administered during the third trimester of pregnancy. In some embodiments, the blocking agent is administered over the length of 4, 8, 12, 16, 20, 24 weeks, as needed.

In a related aspect, the invention provides methods of preventing or reducing the risk of a fetus developing an ASD comprising removing antibodies that bind to one or more fetal biomarkers selected from the group consisting of lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR), from the mother of the fetus.

In some embodiments, antibodies that bind to one, two, three or all biomarkers selected from lactate dehydrogenase (LDH), guanine deaminase (GDA), collapsin response mediator protein 1 (CRMP1) and stress-induced phosphoprotein 1 (STIP1) are removed. In some embodiments, antibodies that bind to one, two or all biomarkers selected from lactate dehydrogenase (LDH), collapsin response mediator protein 1 (CRMP1) and stress-induced phosphoprotein 1 (STIP1) are removed. In some embodiments, antibodies that bind to one, two or all biomarkers selected from guanine deaminase (GDA), collapsin response mediator protein 1 (CRMP1) and stress-induced phosphoprotein 1 (STIP1) are removed. In some embodiments, antibodies that bind to one or both of lactate dehydrogenase (LDH) and collapsin response mediator protein 1 (CRMP1) are removed. In some embodiments, antibodies that bind to one or both of guanine deaminase (GDA) and collapsin response mediator protein 1 (CRMP1) are removed. In some embodiments, antibodies that bind to one or both of lactate dehydrogenase (LDH) and stress-induced phosphoprotein 1 (STIP1) are removed. In some embodiments, antibodies that bind to one or both of guanine deaminase (GDA) and stress-induced phosphoprotein 1 (STIP1) are removed. In some embodiments, antibodies that bind to lactate dehydrogenase (LDH) are removed. In some embodiments, antibodies that bind to guanine deaminase (GDA) are removed. In some embodiments, antibodies that bind to collapsin response mediator protein 1 (CRMP1) are removed. In some embodiments, antibodies that bind to stress-induced phosphoprotein 1 (STIP1) are removed.

In some embodiments, antibodies that bind to one, two, three or all biomarkers selected from lactate dehydrogenase (LDH), guanine deaminase (GDA), dihydropyrimidinase-like protein 2 (DPYSL2) and stress-induced phosphoprotein 1 (STIP1) are removed. In some embodiments, antibodies that bind to one, two or all biomarkers selected from lactate dehydrogenase (LDH), dihydropyrimidinase-like protein 2 (DPYSL2) and stress-induced phosphoprotein 1 (STIP1) are removed. In some embodiments, antibodies that bind to one, two or all biomarkers selected from guanine deaminase (GDA), dihydropyrimidinase-like protein 2 (DPYSL2) and stress-induced phosphoprotein 1 (STIP1) are removed. In some embodiments, antibodies that bind to one or both of lactate dehydrogenase (LDH) and dihydropyrimidinase-like protein 2 (DPYSL2) are removed. In some embodiments, antibodies that bind to one or both of guanine deaminase (GDA) and dihydropyrimidinase-like protein 2 (DPYSL2) are removed. In some embodiments, antibodies that bind to dihydropyrimidinase-like protein 2 (DPYSL2) are removed.

In a related aspect, the invention provides methods of preventing or reducing the risk of a fetus developing an ASD comprising removing antibodies that bind to one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase from the mother of the fetus. The removal of maternal antibodies against one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase can be performed in conjunction with or independently from the removal of the binding of maternal antibodies against the one or more biomarkers described herein.

In some embodiments, the antibodies that bind to the one or more biomarkers are removed from the blood, serum, plasma, or milk.

In some embodiments, the antibodies that bind to the one or more biomarkers are removed from the plasma by plasmapheresis.

In some embodiments, the blood, serum, plasma or milk of the mother is contacted with one or more polypeptides, antigenic fragments thereof, or mimeotopes thereof of one or more fetal biomarkers selected from the group consisting of lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR), attached to a solid support. In some embodiments, the blood, serum, plasma or milk of the mother is contacted with one or more mimeotopes of the one or more biomarkers attached to a solid support.

In some embodiments, polypeptides, antigenic fragments thereof, or mimeotopes thereof of one, two, three or all biomarkers selected from lactate dehydrogenase (LDH), guanine deaminase (GDA), collapsin response mediator protein 1 (CRMP1) and stress-induced phosphoprotein 1 (STIP1) are attached to a solid support and contacted with blood, serum, plasma or milk from the mother. In some embodiments, polypeptides, antigenic fragments thereof, or mimeotopes thereof of one, two or all biomarkers selected from lactate dehydrogenase (LDH), collapsin response mediator protein 1 (CRMP1) and stress-induced phosphoprotein 1 (STIP1) are attached to a solid support and contacted with blood, serum, plasma or milk from the mother. In some embodiments, polypeptides, antigenic fragments thereof, or mimeotopes thereof of one, two or all biomarkers selected from guanine deaminase (GDA), collapsin response mediator protein 1 (CRMP1) and stress-induced phosphoprotein 1 (STIP1) are attached to a solid support and contacted with blood, serum, plasma or milk from the mother. In some embodiments, polypeptides, antigenic fragments thereof, or mimeotopes thereof of one or both of lactate dehydrogenase (LDH) and collapsin response mediator protein 1 (CRMP1) are attached to a solid support and contacted with blood, serum, plasma or milk from the mother. In some embodiments, polypeptides, antigenic fragments thereof, or mimeotopes thereof of one or both of guanine deaminase (GDA) and collapsin response mediator protein 1 (CRMP1) are attached to a solid support and contacted with blood, serum, plasma or milk from the mother. In some embodiments, polypeptides, antigenic fragments thereof, or mimeotopes thereof of one or both of lactate dehydrogenase (LDH) and stress-induced phosphoprotein 1 (STIP1) are attached to a solid support and contacted with blood, serum, plasma or milk from the mother. In some embodiments, polypeptides, antigenic fragments thereof, or mimeotopes thereof of one or both of guanine deaminase (GDA) and stress-induced phosphoprotein 1 (STIP1) are attached to a solid support and contacted with blood, serum, plasma or milk from the mother. In some embodiments, polypeptides, antigenic fragments thereof of lactate dehydrogenase (LDH) are attached to a solid support and contacted with blood, serum, plasma or milk from the mother. In some embodiments, polypeptides, antigenic fragments thereof, or mimeotopes thereof of guanine deaminase (GDA) are attached to a solid support and contacted with blood, serum, plasma or milk from the mother. In some embodiments, polypeptides, antigenic fragments thereof, or mimeotopes thereof of collapsin response mediator protein 1 (CRMP1) are attached to a solid support and contacted with blood, serum, plasma or milk from the mother. In some embodiments, polypeptides, antigenic fragments thereof, or mimeotopes thereof of stress-induced phosphoprotein 1 (STIP1) are attached to a solid support and contacted with blood, serum, plasma or milk from the mother.

In some embodiments, polypeptides, antigenic fragments thereof, or mimeotopes thereof of one, two, three or all biomarkers selected from lactate dehydrogenase (LDH), guanine deaminase (GDA), dihydropyrimidinase-like protein 2 (DPYSL2) and stress-induced phosphoprotein 1 (STIP1) are attached to a solid support and contacted with blood, serum, plasma or milk from the mother. In some embodiments, polypeptides, antigenic fragments thereof, or mimeotopes thereof of one, two or all biomarkers selected from lactate dehydrogenase (LDH), dihydropyrimidinase-like protein 2 (DPYSL2) and stress-induced phosphoprotein 1 (STIP1) are attached to a solid support and contacted with blood, serum, plasma or milk from the mother. In some embodiments, polypeptides, antigenic fragments thereof, or mimeotopes thereof of one, two or all biomarkers selected from guanine deaminase (GDA), dihydropyrimidinase-like protein 2 (DPYSL2) and stress-induced phosphoprotein 1 (STIP1) are attached to a solid support and contacted with blood, serum, plasma or milk from the mother. In some embodiments, polypeptides, antigenic fragments thereof, or mimeotopes thereof of one or both of lactate dehydrogenase (LDH) and dihydropyrimidinase-like protein 2 (DPYSL2) are attached to a solid support and contacted with blood, serum, plasma or milk from the mother. In some embodiments, polypeptides, antigenic fragments thereof, or mimeotopes thereof of one or both of guanine deaminase (GDA) and dihydropyrimidinase-like protein 2 (DPYSL2) are attached to a solid support and contacted with blood, serum, plasma or milk from the mother. In some embodiments, polypeptides, antigenic fragments thereof, or mimeotopes thereof of dihydropyrimidinase-like protein 2 (DPYSL2) are attached to a solid support and contacted with blood, serum, plasma or milk from the mother.

In some embodiments, the LDH is at least one of LDH-A and LDH-B.

The antibodies that bind to the one or more biomarkers described herein can be removed from the mother anytime during pregnancy. In some embodiments, the antibodies that bind to the one or more biomarkers described herein are removed after the fetal brain has begun to develop, e.g., after about the $12^{th}$ week of gestation. In some embodiments, the antibodies that bind to the one or more biomarkers described herein are removed during the second trimester of pregnancy. In some embodiments, the antibodies that bind to the one or more biomarkers described herein are removed during the third trimester of pregnancy. In some embodiments, the antibodies that bind to the one or more biomarkers described herein are removed over the length of 4, 8, 12, 16, 20, 24 weeks, as needed.

Further embodiments of the invention are as described herein.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 3rd ed. (2001) Cold Spring Harbor Laboratory Press, Cold Spring Harbor, N.Y. and Ausubel, ed., Current Protocols in Molecular Biology, 1990-2008, John Wiley Interscience), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The terms "autism spectrum disorder," "autistic spectrum disorder," "autism" or "ASD" interchangeably refer to a spectrum of neurodevelopmental disorders characterized by impaired social interaction and communication accompanied by repetitive and stereotyped behavior. Autism includes a spectrum of impaired social interaction and communication, however, the disorder can be roughly categorized into "high functioning autism" or "low functioning autism," depending on the extent of social interaction and communication impairment. Individuals diagnosed with "high functioning autism" have minimal but identifiable social interaction and communication impairments (i.e., Asperger's syndrome). Additional information on autism spectrum disorders can be found in, for example, *Autism Spectrum Disorders: A Research Review for Practitioners*, Ozonoff, et al., eds., 2003, American Psychiatric Pub; Gupta, *Autistic Spectrum Disorders in Children*, 2004, Marcel Dekker Inc; Hollander, *Autism Spectrum Disorders*, 2003, Marcel Dekker Inc; *Handbook of Autism and Developmental Disorders*, Volkmar, ed., 2005, John Wiley; Sicile-Kira and Grandin, *Autism Spectrum Disorders: The Complete Guide to Understanding Autism, Asperger's Syndrome, Pervasive Developmental Disorder, and Other ASDs*, 2004, Perigee Trade; and Duncan, et al., *Autism Spectrum Disorders [Two Volumes]: A Handbook for Parents and Professionals*, 2007, Praeger.

The terms "lactate dehydrogenase" or "LDH" interchangeably refer to an enzyme that catalyses the interconversion of pyruvate and lactate with concomitant interconversion of NADH and NAD+. Lactate dehydrogenases exist in four distinct enzyme classes. Two of them are cytochrome c-dependent enzymes with each acting on either D-lactate (EC 1.1.2.4) or L-lactate (EC 1.1.2.3). The other two are NAD(P)-dependant enzymes with each acting on either D-lactate (EC 1.1.1.28) or L-lactate (EC 1.1.1.27). The LDH enzyme is composed of 4 subunits, wherein the subunits are either "M" or "H". The LDHA gene encodes the M subunit, known interchangeably LDH-M or LDH-A. The LDHB gene encodes the H subunit, known interchangeably as LDH-H or LDH-B. There are five LDH isozymes, each containing four subunits. The major LDH isozyme of skeletal muscle and liver, LDH-5 ($M_4$), has four muscle (M) subunits; while LDH-1 ($H_4$) is the main isozyme for heart muscle in most species, containing 4 heart (H) subunits. The other variants contain both types of subunits, e.g., LDH-2 ($H_3M_1$)—in the reticuloendothelial system, LDH-3 ($H_2M_2$)—in the lungs, and LDH-4 ($H_1M_3$)—in the kidneys. LDH-2 is the predominant form in the serum. LDHA is also known as LDH1, LDH muscle subunit, LDH-M, EC 1.1.1.27, Renal carcinoma antigen NY-REN-59, Cell proliferation-inducing gene 19 protein, PIG19 and L-lactate dehydrogenase A chain; LDHB is also known as LDH2 or LDH-H or TRG-5; LDHC is testis specific.

Structurally, an LDH-A amino acid sequence has at least about 90%, 91%, 92%, 93%, 94%, 95%, 96%, 97%, 98%, 99% or 100% sequence identity with the amino acid sequence, e.g., of GenBank accession no. AAP36496.1; BAD96798.1; NM_005566.3→NP_005557.1 (isoform 1); NM_001135239.1→NP_001128711.1 (isoform 2); NM_001165414.1→NP_001158886.1 (isoform 3); NM_001165415.1→NP_001158887.1(isoform 4); or NM_001165416.1→NP_001158888.1 (isoform 5) over a sequence length of at least 50, 100, 150, 200, 250, 300, 350 amino acids or over the full length of the polypeptide. Structurally, an LDH-A nucleic acid sequence has at least about 90%, 91%, 92%, 93%, 94%, 95%, 96%, 97%, 98%, 99% or 100% sequence identity with the nucleic acid sequence, e.g., of GenBank accession no. BC067223; CR604911; BC051361; X02152.1; NM_005566.3→NP_005557.1 (isoform 1); NM_001135239.1→NP_001128711.1 (isoform 2); NM_001165414.1→NP_001158886.1 (isoform 3); NM_001165415.1→NP_001158887.1 (isoform 4); or NM_001165416.1→NP_001158888.1 (isoform 5) over a sequence length of at least 300, 500, 750, 1000 nucleic acids or over the full length of the polynucleotide. The sequence alignments can be performed using any alignment algorithm known in the art, e.g., BLAST, ALIGN, set to default settings.

Structurally, an LDH-B amino acid sequence has at least about 90%, 91%, 92%, 93%, 94%, 95%, 96%, 97%, 98%, 99% or 100% sequence identity with the amino acid sequence, e.g., of GenBank accession no. NM_002300.6→NP_002291.1 (variant 1); or NM_001174097.1→NP_001167568.1 (variant 2) over a sequence length of at least 50, 100, 150, 200, 250, 300, 350 amino acids or over the full length of the polypeptide. Structurally, an LDH-B nucleic acid sequence has at least about 90%, 91%, 92%, 93%, 94%, 95%, 96%, 97%, 98%, 99% or 100% sequence identity with the nucleic acid sequence, e.g., of GenBank accession no. BC002361.1; Y00711.1; NM_002300.6→NP_002291.1 (variant 1); or NM_001174097.1→NP_001167568.1 (variant 2) over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "collapsin response mediator protein 1" or "CRMP1" (also known as DRP1; DRP-1; CRMP-1; DPYSL1; ULIP-3) refer to a cytosolic phosphoprotein known to function in neuronal differentiation and axonal guidance. CRMP1 is a member of a family of cytosolic phosphoproteins expressed exclusively in the nervous system. The encoded protein is thought to be a part of the semaphorin signal transduction pathway implicated in semaphorin-induced growth cone collapse during neural development. Alternative splicing results in multiple transcript variants. Structurally, a CRMP1 amino acid sequence has at least about 90%, 91%, 92%, 93%, 94%, 95%, 96%, 97%, 98%, 99% or 100% sequence identity with the amino acid sequence, e.g., of GenBank accession no. NM_001014809.1→NP_001014809.1 (isoform 1) or NM_001313.3→NP_001304.1 (isoform 2), over a sequence length of at least 50, 100, 150, 200, 250, 300, 350 amino acids or over the full length of the polypeptide. Structurally, a CRMP1 nucleic acid sequence has at least about 90%, 91%, 92%, 93%, 94%, 95%, 96%, 97%, 98%, 99% or 100% sequence identity with the nucleic acid sequence, e.g., of GenBank accession no. NM_001014809.1→NP_001014809.1 (isoform 1) or NM_001313.3→NP_001304.1 (isoform 2), over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "Stress Induced Phosphoprotein 1" or "STIP1" (also known as Hsp70/Hsp90-organizing Protein (HOPI), STI1, STILL IEF-SSP-3521 and P60) refers to an adaptor protein that assists in folding of HSP70 and HSP90. STIP1 also stimulates the ATPase activity of HSP70, while inhibiting the ATPase activity of HSP90, suggesting a regulatory role. Furthermore, STIP1 binds to the cellular prion protein PrPc and regulates short-term and long-term memory consolidation. Structurally, a STIP1 amino acid sequence has at least about 90%, 91%, 92%, 93%, 94%, 95%, 96%, 97%, 98%, 99% or 100% sequence identity with the amino acid sequence, e.g., of GenBank accession no. NM_006819.2→NP_006810.1, over a sequence length of at least 50, 100, 150, 200, 250, 300, 350 amino acids or over the full length of the polypeptide. Structurally, a STIP1 nucleic acid sequence has at least about 90%, 91%, 92%, 93%, 94%, 95%, 96%, 97%, 98%, 99% or 100% sequence identity with the nucleic acid sequence, e.g., of GenBank accession no. NM_006819.2→NP_006810.1, over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "guanine deaminase" and "GDA" (also known as Cypin, Guanase, KIAA1258, MGC9982 and Nedasin) refers to an enzyme that catalyzes the hydrolytic deamination of guanine, yielding xanthine and ammonia. GDA has also been shown to regulate PSD-95 postsynaptic targeting. Structurally, a GDA amino acid sequence has at least about 90%, 91%, 92%, 93%, 94%, 95%, 96%, 97%, 98%, 99% or 100% sequence identity with the amino acid sequence, e.g., of GenBank accession no. NM_004293.3→NP_004284.1, over a sequence length of at least 50, 100, 150, 200, 250, 300, 350 amino acids or over the full length of the polypeptide. Structurally, a GDA nucleic acid sequence has at least about 90%, 91%, 92%, 93%, 94%, 95%, 96%, 97%, 98%, 99% or 100% sequence identity with the nucleic acid sequence, e.g., of GenBank accession no. NM_004293.3→NP_004284.1, over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "Dihydropyrimidinase-like Protein 2" or "DPYSL2" (also known as CRMP-2 or CRMP2) refer to a protein involved in axonal guidance by mediating the repulsive effect of Sema3A in axons during axonal specification. Structurally, a DPYSL2 amino acid sequence has at least about 90%, 91%, 92%, 93%, 94%, 95%, 96%, 97%, 98%, 99% or 100% sequence identity with the amino acid sequence, e.g., of GenBank accession no. NM_001386.4→NP_001377.1 or BAD92432, over a sequence length of at least 50, 100, 150, 200, 250, 300, 350 amino acids or over the full length of the polypeptide. Structurally, a DPYSL2 nucleic acid sequence has at least about 90%, 91%, 92%, 93%, 94%, 95%, 96%, 97%, 98%, 99% or 100% sequence identity with the nucleic acid sequence, e.g., of GenBank accession no. NM_001386.4→NP_001377.1, over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "alpha subunit of the barbed-end actin binding protein Cap Z" or "capping protein (actin filament) muscle Z-line, alpha 2" or "CAPZA2" (also known as CAPPA2, CAPZ) refer to a member of the F-actin capping protein alpha subunit family. CAPZA2 is the alpha subunit of the barbed-end actin binding protein Cap Z. By capping the barbed end of actin filaments, Cap Z regulates the growth of the actin filaments at the barbed end. Structurally, a CAPZA2 amino acid sequence has at least about 90%, 91%, 92%, 93%, 94%, 95%, 96%, 97%, 98%, 99% or 100% sequence identity with the amino acid sequence, e.g., of GenBank accession no. NM_006136.2→NP_006127.1, over a sequence length of at least 50, 100, 150, 200, 250, 300, 350 amino acids or over the full length of the polypeptide. Structurally, a CAPZA2 nucleic acid sequence has at least about 90%, 91%, 92%, 93%, 94%, 95%, 96%, 97%, 98%, 99% or 100% sequence identity with the nucleic acid sequence, e.g., of GenBank accession no. NM_006136.2→NP_006127.1, over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "Y Box Binding Protein 1" or "YBX1" (also known as BP-8, CSDA2, CSDB, DBPB, MDR-NF1, MGC104858, MGC110976, MGC117250, NSEP-1, NSEP1, YB1 and YB1) refers to a protein that mediates pre-mRNA alternative splicing regulation. YBX1 binds to splice sites in pre-mRNA and regulates splice site selection; binds and stabilizes cytoplasmic mRNA; contributes to the regulation of translation by modulating the interaction between the mRNA and eukaryotic initiation factors; binds to promoters that contain a Y-box (5'-CTGATTGGCCAA-3'; SEQ ID NO:1), e.g., found in HLA class II genes; and promotes the separation of DNA strands that contain mismatches or are modified by cisplatin. Structurally, a YBX1 amino acid sequence has at least about 90%, 91%, 92%, 93%, 94%, 95%, 96%, 97%, 98%, 99% or 100% sequence identity with the amino acid sequence, e.g., of GenBank accession no. NM_004559.3→NP_004550.2, over a sequence length of at least 50, 100, 150, 200, 250, 300, 350 amino acids or over the full length of the polypeptide. Structurally, a YBX1 nucleic acid sequence has at least about 90%, 91%, 92%, 93%, 94%, 95%, 96%, 97%, 98%, 99% or 100% sequence identity with the nucleic acid sequence, e.g., of GenBank accession no. NM_004559.3→NP_004550.2, over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "Eukaryotic Translation and Elongation Factor 1A1" and "EEF1A1" refer to an isoform of the alpha subunit of the elongation factor-1 complex that transports aminoacyl tRNA's to the ribosome. The 1A1 isoform is expressed in brain, placenta, lung, liver and pancreas and is an autoantigen in 66% of cases of Felty syndrome. Felty syndrome is characterized by a combination of rheumatoid arthritis, splenomegaly and neutropenia. Structurally, an EEF1A1 amino acid sequence has at least about 90%, 91%, 92%, 93%, 94%, 95%, 96%, 97%, 98%, 99% or 100% sequence identity with the amino acid sequence, e.g., of GenBank accession no. NM_001402.5→NP_001393.1, over a sequence length of at least 50, 100, 150, 200, 250, 300, 350 amino acids or over the full length of the polypeptide. Structurally, an EEF1A1 nucleic acid sequence has at least about 90%, 91%, 92%, 93%, 94%, 95%, 96%, 97%, 98%, 99% or 100% sequence identity with the nucleic acid sequence, e.g., of GenBank accession no. NM_001402.5→NP_001393.1, over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "Microtubule-associated protein Tau" and "MAPT" (also known as DDPAC, FLJ31424, MAPTL, MGC138549, MSTD, MTBT1, MTBT2, PPND and TAU) refer to a protein whose transcript undergoes complex, regulated alternative splicing that leads to a range of different MAPT mRNA transcripts found in neurons based on the maturation state and neuron type. Mutations or deleterious splice variants are associated with neurodegenerative diseases including Alzheimer's disease, Pick's disease, frontotemporal dementia, corticobasal degeneration and progressive supranuclear palsy. Structurally, a MAPT amino acid sequence has at least about 90%, 91%, 92%, 93%, 94%, 95%, 96%, 97%, 98%, 99% or 100% sequence identity with the amino acid sequence, e.g., of GenBank accession no. NM_016835.4→NP_058519.3 (isoform 1); NM_005910.5→NP_005901.2 (isoform 2); NM_016834.4→NP_058518.1 (isoform 3); NM_016841.4→NP_058525.1 (isoform 4); NM_001123067.3→NP_001116539.1 (isoform 5); or NM_001123066.3→NP_001116538.2 (isoform 6), over a sequence length of at least 50, 100, 150, 200, 250, 300, 350 amino acids or over the full length of the polypeptide. Structurally, a MAPT nucleic acid sequence has at least about 90%, 91%, 92%, 93%, 94%, 95%, 96%, 97%, 98%, 99% or 100% sequence identity with the nucleic acid sequence, e.g., of GenBank accession no. NM_016835.4→NP_058519.3 (isoform 1); NM_005910.5→NP_005901.2 (isoform 2); NM_016834.4→NP_058518.1 (isoform 3); NM_016841.4→NP_058525.1 (isoform 4); NM_001123067.3→NP_001116539.1 (isoform 5); or NM_001123066.3→NP_001116538.2 (isoform 6), over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "Dynamin 1-like protein" and "DNM1L" (also known as DLP1, DRP1, DVLP, DYMPLE, HDYNIV and VPS1) refer to a member of the dynamin family of GTPases that plays a role in regulating mitochondrial morphology controlling the distributions of mitochondrial tubules in the cytoplasm. The DNM1L gene produces three alternatively spliced variants which are alternatively polyadenylated. Structurally, a DNM1L amino acid sequence has at least about 90%, 91%, 92%, 93%, 94%, 95%, 96%, 97%, 98%, 99% or 100% sequence identity with the amino acid sequence, e.g., of GenBank accession no. NM_012062.3→NP_036192.2 (isoform 1); NM_012063.2→NP_036193.2 (isoform 2); NM_005690.3→NP_005681.2 (isoform 3), over a sequence length of at least 50, 100, 150, 200, 250, 300, 350 amino acids or over the full length of the polypeptide. Structurally, a DNM1L nucleic acid sequence has at least about 90%, 91%, 92%, 93%, 94%, 95%, 96%, 97%, 98%, 99% or 100% sequence identity with the nucleic acid sequence, e.g., of GenBank accession no. NM_012062.3→NP_036192.2 (isoform 1); NM_012063.2→NP_036193.2 (isoform 2); NM_005690.3→NP_005681.2 (isoform 3), over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "Neurofilament, light polypeptide" and "NEFL" (also known as CMT1F, CMT2E, NF-L and NFL) refer to type IV intermediate filament heteropolymers composed of light, medium, and heavy chains. NEFL is a component of the axoskeleton and functions to maintain neuronal morphology and may play a role in intracellular transport to axons and dendrites. Mutations in NEFL cause Charcot-Marie-Tooth diseases types 1F (CMT1F) and 2E (CMT2E)—both peripheral nervous system disorders. NEFL has also been associated with Parkinson disease and Amyotropic lateral sclerosis (ALS). Structurally, a NEFL amino acid sequence has at least about 90%, 91%, 92%, 93%, 94%, 95%, 96%, 97%, 98%, 99% or 100% sequence identity with the amino acid sequence, e.g., of GenBank accession no. NM_006158.3→NP_006149.2, over a sequence length of at least 50, 100, 150, 200, 250, 300, 350 amino acids or over the full length of the polypeptide. Structurally, a NEFL nucleic acid sequence has at least about 90%, 91%, 92%, 93%, 94%, 95%, 96%, 97%, 98%, 99% or 100% sequence identity with the nucleic acid sequence, e.g., of GenBank accession no. NM_006158.3→NP_006149.2, over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "Radixin" or "RDX" (also known as DFNB24) refers to a cytoskeletal protein involved in linking actin to the plasma membrane. RDX has high sequence identity to Exrin and Moesin. Structurally, a RDX amino acid sequence has at least about 90%, 91%, 92%, 93%, 94%, 95%, 96%, 97%, 98%, 99% or 100% sequence identity with the amino acid sequence, e.g., of GenBank accession no. NM_002906.3→NP_002897.1, over a sequence length of at least 50, 100, 150, 200, 250, 300, 350 amino acids or over the full length of the polypeptide. Structurally, a RDX nucleic acid sequence has at least about 90%, 91%, 92%, 93%, 94%, 95%, 96%, 97%, 98%, 99% or 100% sequence identity with the nucleic acid sequence, e.g., of GenBank accession no. NM_002906.3→NP_002897.1, over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "moesin" and "MSN" and "membrane-organizing extension spike protein" refer to a member of the ERM family which includes ezrin and radixin. ERM proteins function as cross-linkers between plasma membranes and actin-based cytoskeletons. Moesin is localized to filopodia and other membranous protrusions that are important for cell-cell recognition and signaling and for cell movement. Structurally, a MSN amino acid sequence has at least about 90%, 91%, 92%, 93%, 94%, 95%, 96%, 97%, 98%, 99% or 100% sequence identity with the amino acid sequence, e.g., of GenBank accession no. NM_002444.2→NP_002435.1, over a sequence length of at least 50, 100, 150, 200, 250, 300, 350 amino acids or over the full length of the polypeptide. Structurally, a MSN nucleic acid sequence has at least about 90%, 91%, 92%, 93%, 94%, 95%, 96%, 97%, 98%, 99% or 100% sequence identity with the nucleic acid sequence, e.g., of GenBank accession no. NM_002444.2→NP_002435.1, over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The terms "ezrin" and "EZR" (also known as CVL; CVIL; VIL2; MGC1584; FLJ26216; DKFZp762H157) refer to a cytoplasmic peripheral membrane protein that functions as a protein-tyrosine kinase substrate in microvilli. As a member of the ERM protein family, this protein serves as an intermediate between the plasma membrane and the actin cytoskeleton. EZR protein plays a role in cell surface structure adhesion, migration and organization, and has been implicated in various human cancers. Structurally, a EZR amino acid sequence has at least about 90%, 91%, 92%, 93%, 94%, 95%, 96%, 97%, 98%, 99% or 100% sequence identity with the amino acid sequence, e.g., of GenBank accession no. NM_003379.4→NP_003370.2 (isoform 1) or NM_001111077.1→NP_001104547.1 (isoform 2), over a sequence length of at least 50, 100, 150, 200, 250, 300, 350 amino acids or over the full length of the polypeptide. Structurally, a EZR nucleic acid sequence has at least about 90%, 91%, 92%, 93%, 94%, 95%, 96%, 97%, 98%, 99% or 100% sequence identity with the nucleic acid sequence, e.g., of GenBank accession no. NM_003379.4→NP_003370.2 (isoform 1) or NM_001111077.1→NP_001104547.1 (isoform 2), over a sequence length of at least 300, 500, 750, 1000 nucleic acids or over the full length of the polynucleotide. The sequence alignments can be performed using any alignment algorithm known in the art, e.g., BLAST, ALIGN, set to default settings.

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The terms "polypeptide," "peptide," and "protein" are used interchangeably herein to refer to a polymer of amino acid residues, or an assembly of multiple polymers of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, two essentially identical sequences. Because of the degeneracy of the genetic code, a large number of different nucleic acids can encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);

5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The invention provides polypeptides or polynucleotides that are substantially identical to the polypeptides or polynucleotides, respectively, exemplified herein (e.g., a biomarker selected from the group consisting of lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR), and antigenic fragments thereof). Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "antigenic fragment" refers to a contiguous subsequence of a polypeptide that binds to an antibody. An antigenic fragment may or may not be immunogenic, i.e., it may or may not induce an immune response.

The term "conformational antigenic fragment" refers to a spatially contiguous region of a polypeptide or tetramer which may or may not be formed by a contiguous subsequence. A conformational antigenic fragment may or may not be immunogenic.

The term "epitope" or "antigenic determinant" refers to a site on a polypeptide to which B and/or T cells respond. B-cell epitopes can be formed both from contiguous amino acids or noncontiguous amino acids juxtaposed by tertiary or quaternary folding of a protein. Epitopes formed from contiguous amino acids are typically retained on exposure to denaturing solvents whereas epitopes formed by tertiary or quaternary folding (i.e., conformationally determined) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen (e.g., an electrochemiluminescence assay, a competitive ELISA, a solid phase radioimmunoassay (SPRIA) or a blocking Western blot). T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf. Dis.* 170, 1110-19 (1994)), by antigen-dependent killing (cytotoxic T lymphocyte assay, Tigges et al., *J. Immunol.* (1996) 156:3901-3910) or by cytokine secretion. The epitopes of human testis-specific lactate dehydrogenase have been deduced from a cDNA sequence. See, Millan, et al., *Proc. Natl. Acad Sci* (1987) 84(15):5311-5315.

The terms "bind(s) specifically" or "specifically directed against" refers to the preferential association between T-cell receptors and/or antibodies, in whole or part, with a target polypeptide or an antigenic fragment thereof in comparison to other polypeptides. It is, of course, recognized that a certain degree of non-specific interaction may occur between an antibody or T-cell receptor and a non-target polypeptide. Nevertheless, specific binding, may be distinguished as mediated through specific recognition of the target polypeptide or an antigenic fragment thereof. Typically, specific binding or a specifically directed immune response results in a much stronger association between the target polypeptide and an antibody against the target polypeptide or T-cell receptor than between an antibody against the target polypeptide or T-cell receptor and a non-target polypeptide. Specific binding typically results in greater than about 10-fold and most preferably greater than 100-fold increase in amount of bound antibody (per unit time) against the target polypeptide to a cell or tissue bearing the target polypeptide as compared to a cell or tissue lacking an epitope of the target polypeptide. Specific binding between the target polypeptide and an antibody against the target polypeptide generally means an affinity of at least $10^6$ $M^{-1}$. Affinities greater than $10^8$ $M^{-1}$ are preferred. Specific binding can be determined using any assay for antibody binding known in the art, including without limitation, Western blot, dot blot, ELISA, flow cytometry, electrochemiluminescence, multiplex bead assay (e.g., using Luminex or fluorescent microbeads), immunohistochemistry. T-cells specifically directed against an epitope of a target polypeptide typically exhibit antigen-induced proliferation in response to the target polypeptide that is greater than about 2-fold, and more preferably greater than about 5-fold or 10-fold than antigen-induced proliferation in response to a non-target polypeptide. T cell proliferation assays are known in the art can be measured by $^3$H-thymidine incorporation.

The term "titer", when used to refer to maternal antibodies which bind specifically to a target biomarker (e.g., as described herein), indicates a measurement combining the concentration and the specificity of the antibodies in the biological sample, where a threshold titer of antibodies against a target biomarker may be reached through a high concentration of antibodies with a moderate binding constant or dissociation constant or a lower concentration of antibodies with a high binding constant or low dissociation constant.

The term "increased risk of developing an ASD" refers to an increased likelihood or probability that a fetus or child exposed to antibodies that bind to one or more biomarkers described herein (e.g., selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)) or to levels of antibodies against the one or more of the biomarkers above a predetermined threshold level will develop symptoms of an ASD in comparison to the risk, likelihood or probability of a fetus or child that has not been exposed to antibodies against the one or more biomarkers or to levels of antibodies against the one or more biomarkers that are below a predetermined threshold level.

The term "reduced risk of developing an ASD" refers to the decreased likelihood or probability that a fetus or child exposed to antibodies against one or more biomarkers described herein (e.g., selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)) or to levels of antibodies against the one or more of the biomarkers above a predetermined threshold level, and whose mother has received therapeutic intervention, e.g., to block, inactivate or remove antibodies that bind to the biomarkers, will develop symptoms of an ASD in comparison to the likelihood or probability that a fetus or child exposed to antibodies against the biomarkers or to levels of antibodies against the one or more biomarkers above a predetermined threshold level and whose mother has not received therapeutic intervention will develop symptoms of an ASD.

The term "mimeotope" refers to peptides or polypeptides of the one or more biomarkers described herein (e.g., selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)) that imitate an epitope (e.g., bound by an antibody against the biomarker), although no clear homology may exist between the structure or sequence of such mimeotopes and the epitope of the native antigen (e.g., the one or more biomarkers described herein). Instead, mimicry of a mimeotope relies on similarities in physicochemical properties and similar spatial organization. The screening and construction of mimeotopes is known in the art. For example, mimeotopes can be derived from known epitopes by sequence modification or developed de novo using combinatorial peptide libraries for peptides, e.g., that bind to antibodies against the one or more biomarkers. See, e.g., Yip and Ward, *Comb Chem High Throughput Screen* (1999) 2(3):125-128; Sharav, et al, *Vaccine* (2007) 25(16): 3032-37; and Knittelfelder, et al., *Expert Opin Biol Ther* (2009) 9(4):493-506.

The term "familial history" refers to the presence of a disease condition (e.g., an ASD or an autoimmune disease) in a family member. The family member can be of direct lineage, e.g., a parent, a child or a grandparent or a close relation, e.g., a sibling, an aunt or uncle, a cousin. Typically the family member is a blood relative with a common genetic heritage.

The term "therapeutically acceptable amount" or "therapeutically effective dose" interchangeably refer to an amount sufficient to effect the desired result (i.e., a sufficient amount of agent to block binding of antibodies against the biomarker to the target biomarker), with minimal or no side effects. In some embodiments, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of an anti-biomarker antibody blocking agent of the invention can prevent the onset of, or result in a decrease in severity of, respectively, an ASD. A "prophylactically effective dosage," and a "therapeutically effective dosage," can also prevent or ameliorate, respectively, impairment or disability due to the disorders and diseases resulting from activity of maternal anti-biomarker antibodies.

The term "specifically inhibit(s)" refers to the ability of an agent or ligand to inhibit the binding of antibodies against the one or more biomarkers (e.g., selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)) to the one or more biomarkers. Specific inhibition typically results in at least about a 2-fold inhibition over background, for example, greater than about 10-fold, 20-fold, 50-fold inhibition of binding of antibodies against the biomarker to the target biomarker, for example, by comparing the binding of the anti-biomarker antibodies in the absence of the agent. In some embodiments, the binding of anti-biomarker antibodies to the target biomarker is completely inhibited. Typically, specific inhibition is a statistically meaningful reduction in anti-biomarker antibody binding to the target biomarker (e.g., $p \leq 0.05$) using an appropriate statistical test.

The term "agent" as used herein refers to polypeptides (e.g., ligands, antibodies), peptidomimetics, nucleic acids, small organic compounds, and the like.

DETAILED DESCRIPTION

1. Introduction

Figure 1:
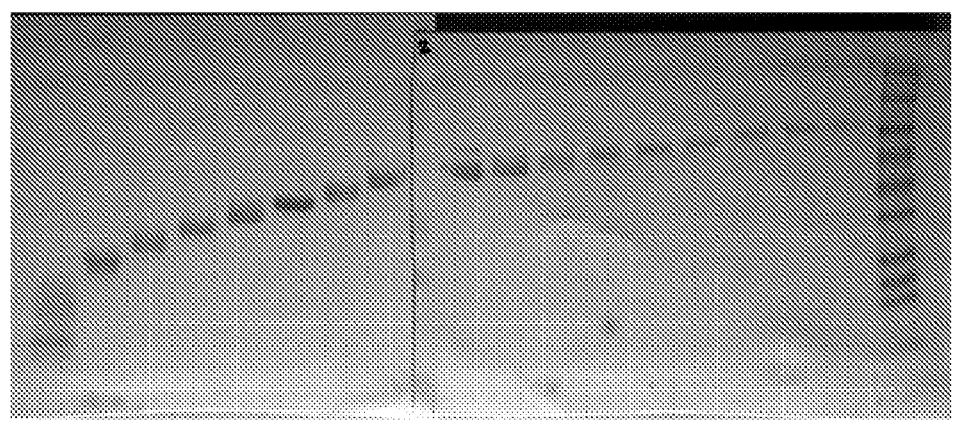
FIG. 1 illustrates a Prep Cell Ponceau and Western blot. (a) Ponceau stained nitrocellulose membrane containing samples from every 6th fraction collected from Prep Cell separation of Rhesus fetal brain protein. (b) Western blots of the membranes in (a) probed with maternal plasma reactive against the 37 kDa, 39 kDa and 73 kDa antigens.
Figure 1:
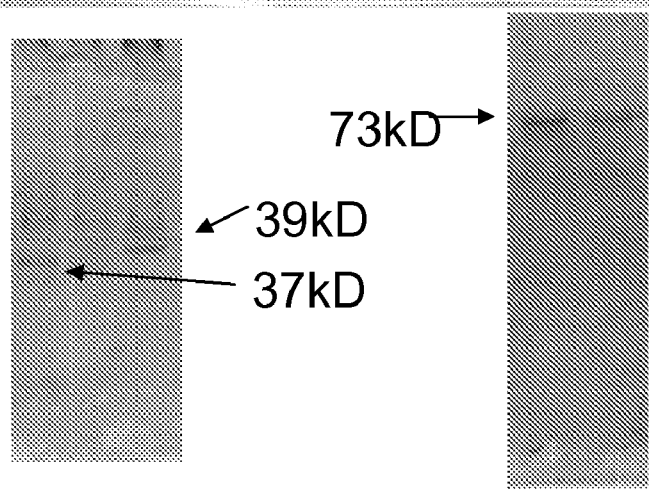

Autism Spectrum Disorders (ASD) are severe neurodevelopmental disorders affecting as many as 1 in 150 children. The presence of maternal IgG antibodies with specificity for human fetal brain proteins at molecular weights of approximately 37 kDa, 39 kDa and 73 kDa in a subset of mothers of children with an ASD has been described. See, e.g., U.S. Pat. No. 7,452,681. The present invention is based, in part, on the identity of biomarkers bound by maternal antibodies that are indicative of an increased risk that a fetus will develop an ASD. Biomarkers with an apparent molecular weight of 37 kDa include lactate dehydrogenase (LDH) and alpha subunit of the barbed-end actin binding protein Cap Z (CAPZA2). Biomarkers with an apparent molecular weight of 39 kDa include guanine deaminase (GDA), Y Box Binding Protein 1 (YBX1), eukaryotic translation and elongation factor 1A1 (EEF1A1), and microtubule-associated protein Tau (MAPT). Biomarkers with an apparent molecular weight of 73 kDa include collapsin response mediator protein 1 (CRMP1), stress-induced phosphoprotein 1 (STIP1), dihydropyrimidinase-like protein 2 (DPYSL2), dynamin 1-like protein (DNM1L), radixin (RDX), moesin (MSN), and ezrin (EZR)). The presence of maternal antibodies against one or more of the identified fetal biomarkers in a biological sample of the mother or potential mother is indicative of an increased risk of the fetus to develop an ASD.

2. Patients Subject to Diagnosis or Treatment

The methods can be performed on any mammal, for example, a human, a non-human primate, a laboratory mammal (e.g., a mouse, a rat, a rabbit, a hamster), a domestic mammal (e.g., a cat, a dog), or an agricultural mammal (e.g., bovine, ovine, porcine, equine). In some embodiments, the patient is a woman and a human.

Any woman capable of bearing a child can benefit from the diagnostic methods of the present invention. The child may or may not be conceived, i.e., the woman can be but need not be pregnant. In some embodiments, the woman has a child who is a neonate. In some embodiments, the woman is of child-bearing age, i.e., she has begun to menstruate and has not reached menopause.

In some embodiments, the diagnostic and prevention and/or treatment methods are performed on a woman carrying a fetus (i.e., who is pregnant). The methods can be performed any time during pregnancy. In some embodiments, the diagnostic and prevention and/or treatment methods are performed on a woman carrying a fetus whose brain has begun to develop. For example, the fetus may at be at about 12 weeks of gestation or later. In some embodiments, the woman subject to treatment or diagnosis is in the second or third trimester of pregnancy. In some embodiments, the woman subject to treatment or diagnosis is in the first trimester of pregnancy. In some embodiments, the woman is post-partum, e.g., within 6 month of giving birth. In some embodiments, the woman is post-partum and breastfeeding.

Women who will benefit from the present diagnostic and prevention and/or treatment methods may but need not have a familial history of an ASD or an autoimmune disease. For example, the woman may have an ASD or have a family member (e.g., a parent, a child, a grandparent) with an ASD. In some embodiments, the woman suffers from an autoimmune disease or has a family member (e.g., a parent, a child, a grandparent) who suffers from an autoimmune disease.

In some embodiments, the diagnosis or prevention/treatment methods comprise the step of determining that the diagnosis and/or prevention/treatment methods are appropriate for the patient, e.g., based on prior medical history or familial medical history or pregnancy status or any other relevant criteria.

3. Methods of Determining the Risk of Developing an Autism Spectrum Disorder The present invention provides methods for determining the likelihood that a fetus or child will develop an autism spectrum disorder (ASD) comprising identifying in a biological sample from the mother of the fetus or child the presence of maternal antibodies that bind to 1, 2, 3, 4, 5, 6, 7, 8, 9, 10, 11, 12, 13, or more, of the biomarkers described herein (e.g., selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)), wherein the presence of maternal antibodies that specifically bind to the one or more biomarkers indicates an increased likelihood of the fetus or child for developing an ASD.

With respect to the biological sample taken from the mother, any fluid sample containing antibodies can be used. For example, the biological sample may be blood, serum, plasma, amniotic fluid, urine, milk or saliva. Of course, one or more different bodily fluids can be evaluated for antibodies that specifically bind to the one or more biomarkers.

The biological sample is evaluated for the presence of antibodies that specifically bind to bind to 1, 2, 3, 4, 5, 6, 7, 8, 9, 10, 11, 12, 13, or more, of the biomarkers (e.g., selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)).

In some embodiments, detection of the presence of anti-biomarker antibodies (versus the absence of detection of anti-biomarker antibodies) indicates an increased probability that the fetus has or will develop an ASD.

In some embodiments, the level or titer of anti-biomarker antibodies in the biological sample is compared to a threshold level or titer. A level or titer of anti-biomarker antibodies in the biological sample that is greater than the threshold level or titer indicates an increased probability that the fetus has or will develop an ASD. Likewise, a level or titer of anti-biomarker antibodies in the biological sample that is less than the threshold level or titer does not indicate an increased probability (i.e., indicates no increased probability) that the fetus has or will develop an ASD. The threshold level or titer for anti-biomarker antibodies in a particular biological fluid can be determined by evaluating levels of anti-biomarker antibodies in populations of pregnant women and comparing the anti-biomarker levels or titer in the biological fluid of the mother when the child developed an ASD and to the anti-biomarker levels or titer in the biological fluid of the mother when the child did not develop an ASD. The threshold levels or titer can also be determined at different time points during pregnancy, e.g., every four weeks, every two weeks or every week during gestation of the fetus. Threshold anti-biomarker levels or titer can also be measured after the child is born, e.g., in the first four weeks after birth and/or while the mother is breastfeeding the child.

The presence or absence of anti-biomarker antibodies or the quantified levels of anti-biomarker antibodies can be determined before, during or after pregnancy. When determined during pregnancy, detection of anti-biomarker antibodies can be performed one, two, three, four or more times, as appropriate, at any time during the course of pregnancy. For example, detection of anti-biomarker antibodies can be made in one or more of the first, second and/or third trimesters of pregnancy. In some embodiments, detection of anti-biomarker antibodies is performed on a biological sample from a woman carrying a fetus whose brain has begun to develop, e.g., after about 12 weeks of gestation. In some embodiments, the presence or absence of anti-biomarker antibodies or the quantified levels of anti-biomarker antibodies are evaluated one or more times post-partum, e.g., in the first four weeks after birth and/or while the mother is breastfeeding the child. In some embodiments, the presence or absence of anti-biomarker antibodies or the quantified levels of anti-biomarker antibodies are evaluated one or more times before pregnancy or in any women who is not pregnant.

The presence of anti-biomarker antibodies may be determined once or more than once, as needed or desired. In some embodiments, the presence or absence of anti-biomarker antibodies or the quantified levels of anti-biomarker antibodies are evaluated every four weeks, every two weeks or every week during pregnancy, or more or less often, as appropriate.

In some embodiments, the test sample is compared to a control. The control can be from the same individual at a different time point. For example, the test sample can be taken during pregnancy, and the control sample can be taken from the same individual before pregnancy. In some instances, the test sample will be taken relatively later in pregnancy term and the control sample will be taken from the same individual earlier in pregnancy term. In this case, if the level of maternal anti-biomarker antibodies is greater in the test sample than in the control sample, then the fetus or child is at an increased risk of developing an ASD. If several samples are evaluated over the course of a pregnancy, increased levels or titers of anti-biomarker antibodies over the term of the pregnancy indicate an increased risk that the fetus or child will develop an ASD. Similarly, absent or decreased levels or titers of anti-biomarker antibodies over the term of the pregnancy indicate a low or reduced risk that the fetus or child will develop an ASD.

The control can also be from a different individual with a known status for the presence of anti-biomarker antibodies. The control can also be a calculated value from a population of individuals with a known status for the presence of anti-biomarker antibodies. The control may be a positive control or a negative control.

In some embodiments, the control is a negative control from another individual or a population of individuals. If the known status of the control sample is negative for anti-biomarker antibodies, then a higher level of maternal anti-biomarker antibodies in the test sample than in the negative control sample indicates that the fetus or child is at an increased risk of developing an ASD. A similar level of maternal anti-biomarker antibodies in the test sample to the negative control sample indicates that the fetus or child is not at an increased risk, i.e., has a low or reduced risk, of developing an ASD.

In some embodiments, the control is a positive control from another individual or a population of individuals, or the control reflects a predetermined threshold level of anti-biomarker antibodies. If the known status of the control sample is positive for anti-biomarker antibodies, then a similar or higher level of maternal anti-biomarker antibodies in the test sample than in the positive control sample indicates that the fetus or child is at an increased risk of developing an ASD. A lower level of maternal anti-biomarker antibodies in the test sample to the control sample indicates that the fetus or child is not at an increased risk or has a low or reduced risk of developing an ASD.

The differences between the control sample or value and the test sample need only be sufficient to be detected. In some embodiments, an increased level of anti-biomarker antibodies in the test sample, and hence an increased risk of an ASD, is determined when the anti-biomarker levels are at least, e.g., 10%, 25%, 50%, 1-fold, 2-fold, 3-fold, 4-fold, or more in comparison to a negative or a prior-measured control.

For the purposes of diagnosing the increased likelihood that a fetus or child will develop an ASD, the presence of maternal antibodies against any subtype, isoform or isozyme of the one or more biomarkers (e.g., selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)) can be determined. For example, the presence or absence of anti-biomarker antibodies or the quantified levels of antibodies against one or both of LDH-A and/or LDH-B can be determined. In some embodiments, the presence or absence of anti-biomarker antibodies or the quantified levels of antibodies against one or more of isozymes LDH-1, LDH-2, LDH-3, LDH-4 and/or LDH-5 are determined.

The anti-biomarker antibodies can be detected using any method known in the art. Exemplary methods include without limitation, Western Blot, Dot Blot, enzyme-linked immunosorbent assay (ELISA), radioimmunoassay (RIA), electrochemiluminescence, multiplex bead assays (e.g., using Luminex or fluorescent microbeads).

The antigen can be a biomarker polypeptide or an antigenic fragment thereof. The biomarker polypeptide or antigenic fragment can be purified or substantially purified from a natural source, or recombinantly or synthetically produced. Methods for the recombinant production of polypeptides are known in the art. See, e.g., Sambrook and Russell, Molecular Cloning: A Laboratory Manual, 3$^{rd}$ Ed., 2001, Cold Spring Harbor Laboratory Press; and Ausubel, et al., Current Protocols in Molecular Biology, 1987-2009, John Wiley Interscience. As discussed above, the cDNA sequences of the biomarkers described herein are known, and can be recombinantly expressed in E. coli. The cDNA sequences of LDH-A and LDH-B are known and have been recombinantly expressed in E. coli and found to maintain the same functional and combinatorial properties as the isoenzymes isolated from human tissue. See, e.g., Barstow, et al., Biochim Biophys Acta. (1990):1087(1):73-9. The identification of antigenic fragments of a polypeptide is also well known in the art. For example, partial length fragments of the biomarker polypeptides can be constructed that are at least 10 amino acids in length. Overlapping peptides can be constructed, e.g., of 10, 20 or 30 amino acids in length, and the immunodominant epitopes of the biomarker polypeptides identified. In some embodiments, the partial length fragments of biomarker polypeptides are at least about 50%, 60%, 70%, 80%, 90%, 95% of the full length of the biomarker polypeptide. In some embodiments, the partial length fragments of the biomarker polypeptides are about 10, 25, 50, 100, 150, 200, 250 or 300 amino acids in length. The partial length fragments can have the N-terminus or the C-terminus of the biomarker polypeptide removed, or part of both of the N-terminus and the C-terminus removed. Partial length fragments of the biomarker polypeptides that find use detectably and specifically are bound by anti-biomarker antibodies from a biological sample of a mother or potential mother, e.g., as detected by any immunoassay. The binding of a partial length biomarker polypeptide or antigenic fragment can be compared to the binding of the full length biomarker polypeptide. The biomarker polypeptide can be from the same or different species as the patient, so long as it can be bound by the maternal antibodies. In some embodiments, the biomarker polypeptide is human.

In some embodiments, the biomarker polypeptide or antigenic fragment thereof has at least about 90%, 93%, 95%, 97%, 99% or 100% sequence identity with a biomarker polypeptide as described herein, e.g., with a LDHA amino acid sequence of GenBank Accession No. AAP36496.1; BAD96798.1; NP_005557.1 (isoform 1); NP_001128711.1 (isoform 2); NP_001158886.1 (isoform 3); NP_001158887.1 (isoform 4); or NP_001158888.1 (isoform 5); with a LDHB. amino acid sequence of GenBank Accession No. NP_002291.1 (variant 1); or NP_001167568.1 (variant 2); with a CRMP1 amino acid sequence of GenBank Accession No. NP_001014809.1 (isoform 1) or NP_001304.1 (isoform 2); with a STIP1 amino acid sequence of GenBank Accession No. NP_006810.1; with a GDA amino acid sequence of GenBank Accession No. NP_004284.1; with a DPYSL2 amino acid sequence of GenBank Accession No. NP_001377.1 or BAD92432; with a CAPZA2 amino acid sequence of GenBank Accession No. NP_006127.1; with an YBX1 amino acid sequence of GenBank Accession No. NP_004550.2; with an EEF1A1 amino acid sequence of GenBank Accession No. NP_001393.1; with MAPT amino acid sequence of GenBank Accession No. NP_058519.3 (isoform 1); NP_005901.2 (isoform 2); NP_058518.1 (isoform 3); NP_058525.1 (isoform 4); NP_001116539.1 (isoform 5); or NP_001116538.2 (isoform 6); with a DNM1L amino acid sequence of GenBank Accession No. NP_036192.2 (isoform 1); NP_036193.2 (isoform 2); NP_005681.2 (isoform 3); with a NEFL amino acid sequence of GenBank Accession No. NP_006149.2; with a RDX amino acid sequence of GenBank Accession No. NP_002897.1; with a MSN amino acid sequence of GenBank Accession No. NP_002435.1; or with an EZR amino acid sequence of GenBank Accession No. NP_003370.2 (isoform 1) or NP_001104547.1 (isoform 2).

In some embodiments, the antigen used to detect anti-biomarker antibodies in a biological sample from a mother or potential mother is a mimeotope of the biomarker. The biomarker mimeotope can be derived from a known antigenic epitope of the biomarker, with one or more amino acids substituted, deleted or added. The biomarker mimeotope can be designed or identified de novo, by screening a peptide library for mimeotopes that bind to anti-biomarker antibodies.

In some embodiments, the antigen used to detect anti-biomarker antibodies, e.g., a biomarker polypeptide or antigenic fragment thereof, or a biomarker mimeotope, can be immobilized on a solid support. The solid support can be, for example, a multiwell plate, a microarray chip, a bead, a porous strip, a nitrocellulose filter. The immobilization can be via covalent or non-covalent binding. In some embodiments, the immobilization is through a capture antibody that specifically binds to the target biomarker. Monoclonal antibodies against LDH and antigen-capture immunoassays for LDH have been developed. See, e.g., Wang and Smith, J Food Science (1995) 60(2):253; and Druilhe, et al., Am J Trop Med Hyg (2001) 64(5,6)233-241. Commercially available polyclonal antibodies for LDH (Abcam, Cambridge, Mass.), GDA (Sigma), YBX1 (Abcam), CRMP1 (Abcam) STIP1 (Abcam) and Ezrin/Radixin/Moesin (Cell Signalling) can be used to create antigen-capture assays. Purified native LDH (Cell Sciences, Canton, Mass.), recombinant full length GDA (Abnova, Taipei, Taiwan), recombinant full length YBX1 (Abnova), recombinant full length CAPZA2 (Abnova), recombinant full length DPYSL2 (Novus Biologicals), recombinant full length DNM1L (Abnova), recombinant full length EEF1A1 (Abnova), recombinant full length MAPT (Abnova), recombinant full length NEFL (Abnova), recombinant full length CRMP1 (OriGene, Rockville, Md.) and recombinant full length STIP1 (Abnova) human proteins can be immobilized on a soild support and used as an anti-biomarker antibody assay.

For detection of the maternal anti-biomarker antibodies, a sample is incubated with a biomarker polypeptide, antigenic fragments thereof or a biomarker mimeotope under conditions (i.e., time, temperature, concentration of sample) sufficient to allow specific binding of any antibodies or autoantibodies present in the sample. The biomarker polypeptide, antigenic fragments thereof or biomarker mimeotope can be bound to a solid support. For example, the biomarker polypeptide, antigenic fragments thereof or biomarker mimeotope can be exposed to a sample for about 0.5, 1.0, 1.5, 2.0, 2.5, 3.0 hours, or overnight, about 8, 10 or 12 hours. However, incubation time can be more or less depending on, e.g., the composition of the antigen, the dilution of the sample and the temperature for incubation. Incubations using less diluted samples and higher temperatures can be carried out for shorter periods of time. Incubations are usually carried out at room temperature (about 25° C.) or at biological temperature (about 37° C.), and can be carried out in a refrigerator (about 4° C.). Washing to remove unbound sample before addition of a secondary antibody is carried according to known immunoassay methods.

Labeled secondary antibodies are generally used to detect antibodies or autoantibodies in a sample that have bound to one or more biomarker polypeptides, antigenic fragments thereof or biomarker mimeotopes. Secondary antibodies bind to the constant or "C" regions of different classes or isotypes of immunoglobulins—IgM, IgD, IgG, IgA, and IgE. Usually, a secondary antibody against an IgG constant region is used in the present methods. Secondary antibodies against the IgG subclasses, for example, IgG1, IgG2, IgG3, and IgG4, also find use in the present methods. Secondary antibodies can be labeled with any directly or indirectly detectable moiety, including a fluorophore (i.e., fluoroscein, phycoerythrin, quantum dot, Luminex bead, fluorescent bead), an enzyme (i.e., peroxidase, alkaline phosphatase), a radioisotope (i.e., $^3$H, $^{32}$P, $^{125}$I) or a chemiluminescent moiety. Labeling signals can be amplified using a complex of biotin and a biotin binding moiety (i.e., avidin, streptavidin, neutravidin). Fluorescently labeled anti-human IgG antibodies are commercially available from Molecular Probes, Eugene, Oreg. Enzyme-labeled anti-human IgG antibodies are commercially available from Sigma-Aldrich, St. Louis, Mo. and Chemicon, Temecula, Calif.

The method of detection of the presence or absence, or differential presence, of antibodies or autoantibodies in a sample will correspond with the choice of label of the secondary antibody. For example, if the biomarker polypeptide or antigenic fragments thereof are transferred onto a membrane substrate suitable for immunoblotting, the detectable signals (i.e., blots) can be quantified using a digital imager if enzymatic labeling is used or an x-ray film developer if radioisotope labeling is used. In another example, if the biomarker polypeptide or antigenic fragments thereof are transferred to a multi-well plate, the detectable signals can be quantified using an automated plate reader capable of detecting and quantifying fluorescent, chemiluminescent, and/or colorimetric signals. Such methods of detection are well known in the art.

General immunoassay techniques are well known in the art. Guidance for optimization of parameters can be found in, for example, Wu, *Quantitative Immunoassay: A Practical Guide for Assay Establishment, Troubleshooting, and Clinical Application*, 2000, AACC Press; *Principles and Practice of Immunoassay*, Price and Newman, eds., 1997, Groves Dictionaries, Inc.; *The Immunoassay Handbook*, Wild, ed., 2005, Elsevier Science Ltd.; Ghindilis, Pavlov and Atanassov, *Immunoassay Methods and Protocols*, 2003, Humana Press; Harlow and Lane, *Using Antibodies: A Laboratory Manual*, 1998, Cold Spring Harbor Laboratory Press; and *Immunoassay Automation: An Updated Guide to Systems*, Chan, ed., 1996, Academic Press.

The presence or increased presence of maternal anti-biomarker antibodies is indicated by a detectable signal (i.e., a blot, fluorescence, chemiluminescence, color, radioactivity) in an immunoassay, where the biological sample from the mother or potential mother is contacted with a biomarker polypeptide, antigenic fragment thereof or a mimeotope. This detectable signal can be compared to the signal from a control sample or to a threshold value. In some embodiments, increased presence is detected, and an increased risk of ASD is indicated, when the detectable signal of anti-biomarker antibodies in the test sample is at least about 10%, 20%, 30%, 50%, 75% greater in comparison to the signal of anti-biomarker antibodies in the control sample or the predetermined threshold value. In some embodiments, an increased presence is detected, and an increased risk of ASD is indicated, when the detectable signal of anti-biomarker antibodies in the test sample is at least about 1-fold, 2-fold, 3-fold, 4-fold or more, greater in comparison to the signal of anti-biomarker antibodies in the control sample or the predetermined threshold value.

In some embodiments, the results of the anti-biomarker antibody determinations are recorded in a tangible medium. For example, the results of the present diagnostic assays (e.g., the observation of the presence or increased presence of anti-biomarker antibodies) and the diagnosis of whether or not an increased risk of ASD is determined can be recorded, e.g., on paper or on electronic media (e.g., audio tape, a computer disk, a CD, a flash drive, etc.).

In some embodiments, the methods further comprise the step of providing the diagnosis to the patient of whether or not there is an increased risk that the fetus or child will develop an ASD based on the results of the anti-biomarker antibody determinations.

In some embodiments, the methods further comprise the step of administering to the mother or potential mother a therapeutic or preventative regime of one or more blocking agents to reduce, inhibit or prevent binding of anti-biomarker antibodies to 1, 2, 3, 4, 5, 6, 7, 8, 9, 10, 11, 12, 13, or more, of the biomarkers described herein (e.g., selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)).

In a further aspect, the invention provides methods of determining a risk to an offspring, e.g., fetus or child, of developing an autism spectrum disorder (ASD) or determining a risk that a mother or potential mother will bear a child who will develop an autism spectrum disorder (ASD) by identifying in a biological sample from the mother of the offspring the presence of maternal antibodies that specifically bind to one or more proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase, wherein the presence of maternal antibodies that specifically bind to the one or more proteins indicates an increased risk of the offspring for developing an ASD. The determination of the presence of maternal antibodies against one or more proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase can be performed in conjunction with or independently from the determination of maternal antibodies against one or more of the biomarkers described herein. Further embodiments of the diagnostic methods are as described herein.

4. Methods of Reducing Risk by Administering an Anti-Biomarker Antibody Blocking Agent(s)

The invention further provides methods for preventing and/or reducing the risk of developing an ASD in a fetus or child by administering in vivo to the mother an agent or plurality of agents that blocks the binding of the maternal antibodies to 1, 2, 3, 4, 5, 6, 7, 8, 9, 10, 11, 12, 13, or more, of the biomarkers described herein (e.g., selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)).

The prevention and/or treatment methods using an anti-biomarker antibody blocking agent or plurality of agents can be provided to a woman before, during or after pregnancy. In some embodiments, the anti-biomarker antibody blocking agent(s) can be administered one, two, three, four or more times, as appropriate, at any time during the course of pregnancy. For example, the anti-biomarker antibody blocking agent(s) can be administered in one or more of the first, second and/or third trimesters of pregnancy. In some embodiments, the anti-biomarker antibody blocking agent(s) are administered to a woman carrying a fetus whose brain has begun to develop, e.g., after about 12 weeks of gestation. In some embodiments, the anti-biomarker antibody blocking agent(s) are administered one or more times post-partum, e.g., in the first four weeks after birth and/or while the mother is breastfeeding the child. In some embodiments, the anti-biomarker antibody blocking agent(s) are administered one or more times before pregnancy, for example, in a woman who has tested positive for anti-biomarker antibodies and who is trying to become pregnant.

The anti-biomarker antibody blocking agent(s) can be a biomarker polypeptide or an antigenic fragment thereof. The biomarker polypeptide or antigenic fragment can be purified or substantially purified from a natural source, or recombinantly or synthetically produced, as discussed above. For example, partial length fragments of the one or more biomarker polypeptides can be administered that are at least 10 amino acids in length and which are bound by anti-biomarker antibodies. In some embodiments, the partial length fragments of the one or more biomarkers that are administered are at least about 50%, 60%, 70%, 80%, 90%, 95% of the full length of the biomarker polypeptide. In some embodiments, the partial length fragments of the biomarker are about 50, 100, 150, 200, 250 or 300 amino acids in length. The partial length fragments can have the N-terminus or the C-terminus of biomarker polypeptide removed, or part of both of the N-terminus and the C-terminus removed. Partial length fragments of the one or more biomarker polypeptides that find use are bound by anti-biomarker antibodies in the mother or potential mother. In some embodiments, one or more of an LDH-A and/or an LDH-B polypeptide is administered.

In some embodiments, one or more isozymes of an LDH-1, LDH-2, LDH-3, LDH-4 and/or LDH-5 are administered. In some embodiments, the LDH polypeptide or antigenic fragment thereof has at least about 90%, 93%, 95%, 97%, 99% or 100% sequence identity with an LDH polypeptide as described herein, e.g., with an amino acid sequence of GenBank Accession No. NP_001128711, NP_005557.1, AAP36496.1, BAD96798.1, or NP_002291.1.

In some embodiments, the administered biomarker polypeptide or antigenic fragment thereof has at least about 90%, 93%, 95%, 97%, 99% or 100% sequence identity with a biomarker polypeptide as described herein, e.g., with a LDHA amino acid sequence of GenBank Accession No. AAP36496.1; BAD96798.1; NP_005557.1 (isoform 1); NP_001128711.1 (isoform 2); NP_001158886.1 (isoform 3); NP_001158887.1 (isoform 4); or NP_001158888.1 (isoform 5); with a LDHB. amino acid sequence of GenBank Accession No. NP_002291.1 (variant 1); or NP_001167568.1 (variant 2); with a CRMP1 amino acid sequence of GenBank Accession No. NP_001014809.1 (isoform 1) or NP_001304.1 (isoform 2); with a STIP1 amino acid sequence of GenBank Accession No. NP_006810.1; with a GDA amino acid sequence of GenBank Accession No. NP_004284.1; with a DPYSL2 amino acid sequence of GenBank Accession No. NP_001377.1 or BAD92432; with a CAPZA2 amino acid sequence of GenBank Accession No. NP_006127.1; with an YBX1 amino acid sequence of GenBank Accession No. NP_004550.2; with an EEF1A1 amino acid sequence of GenBank Accession No. NP_001393.1; with MAPT amino acid sequence of GenBank Accession No. NP_058519.3 (isoform 1); NP_005901.2 (isoform 2); NP_058518.1 (isoform 3); NP_058525.1 (isoform 4); NP_001116539.1 (isoform 5); or NP_001116538.2 (isoform 6); with a DNM1L amino acid sequence of GenBank Accession No. NP_036192.2 (isoform 1); NP_036193.2 (isoform 2); NP_005681.2 (isoform 3); with a NEFL amino acid sequence of GenBank Accession No. NP_006149.2; with a RDX amino acid sequence of GenBank Accession No. NP_002897.1; with a MSN amino acid sequence of GenBank Accession No. NP_002435.1; or with an EZR amino acid sequence of GenBank Accession No. NP_003370.2 (isoform 1) or NP_001104547.1 (isoform 2).

In some embodiments, a plurality of agents comprising two or more antigenic epitopes of the biomarkers described herein are administered. The plurality of agents can be administered separately or together. The plurality of agents can be a pool of individual peptides. In some embodiments, two or more peptides of different biomarker epitopes are chemically linked. The multiple antigenic epitopes can be from the same or different biomarker polypeptides. Chemical linkage in this case may be by direct linking of the biomarker epitopes or linkage through the use of a chemical scaffold or linker. In some embodiments, two or more peptides of different biomarker epitopes are fused together. The epitope fusions can be expressed recombinantly or chemically synthesized.

In some embodiments, the anti-biomarker antibody blocking agent(s) can be a non-peptide small molecule, i.e., a "small organic molecule", which interferes with or is a bound by anti-biomarker antibodies. This small molecule may act directly on the anti-biomarker antibody or indirectly by facilitating the specific clearance of anti-biomarker antibodies already bound to other agent(s), including antigenic peptides.

In some embodiments, the anti-biomarker antibody blocking agent(s) is one or more mimeotopes of the target biomarker(s). The biomarker mimeotope can be derived from known antigenic epitope(s) of the one or more, with one or more amino acids substituted, deleted or added. The biomarker mimeotope can be designed or identified de novo, or by screening a peptide or small molecule library for mimeotopes that bind to antibodies against the one or more biomarkers.

In some embodiments, polypeptides or mimeotopes that block the binding of maternal antibodies to one, two, three or all biomarkers selected from lactate dehydrogenase (LDH), guanine deaminase (GDA), collapsin response mediator protein 1 (CRMP1) and stress-induced phosphoprotein 1 (STIP1) is administered. In some embodiments, polypeptides or mimeotopes that block the binding of maternal antibodies to one, two or all biomarkers selected from lactate dehydrogenase (LDH), collapsin response mediator protein 1 (CRMP1) and stress-induced phosphoprotein 1 (STIP1) is administered. In some embodiments, polypeptides or mimeotopes that block the binding of maternal antibodies to one, two or all biomarkers selected from guanine deaminase (GDA), collapsin response mediator protein 1 (CRMP1) and stress-induced phosphoprotein 1 (STIP1) is administered. In some embodiments, polypeptides or mimeotopes that block the binding of maternal antibodies to one or both of lactate dehydrogenase (LDH) and collapsin response mediator protein 1 (CRMP1) is administered. In some embodiments, polypeptides or mimeotopes that block the binding of maternal antibodies to one or both of guanine deaminase (GDA) and collapsin response mediator protein 1 (CRMP1) is administered. In some embodiments, polypeptides or mimeotopes that block the binding of maternal antibodies to one or both of lactate dehydrogenase (LDH) and stress-induced phosphoprotein 1 (STIP1) is administered. In some embodiments, polypeptides or mimeotopes that block the binding of maternal antibodies to one or both of guanine deaminase (GDA) and stress-induced phosphoprotein 1 (STIP1) is administered. In some embodiments, polypeptides or mimeotopes that block the binding of maternal antibodies to lactate dehydrogenase (LDH) is administered. In some embodiments, polypeptides or mimeotopes that block the binding of maternal antibodies to guanine deaminase (GDA) is administered. In some embodiments, polypeptides or mimeotopes that block the binding of maternal antibodies to collapsin response mediator protein 1 (CRMP1) is administered. In some embodiments, polypeptides or mimeotopes that block the binding of maternal antibodies to stress-induced phosphoprotein 1 (STIP1) is administered.

In some embodiments, polypeptides or mimeotopes that block the binding of maternal antibodies to one, two, three or all biomarkers selected from lactate dehydrogenase (LDH), guanine deaminase (GDA), dihydropyrimidinase-like protein 2 (DPYSL2) and stress-induced phosphoprotein 1 (STIP1) is administered. In some embodiments, polypeptides or mimeotopes that block the binding of maternal antibodies to one, two or all biomarkers selected from lactate dehydrogenase (LDH), dihydropyrimidinase-like protein 2 (DPYSL2) and stress-induced phosphoprotein 1 (STIP1) is administered. In some embodiments, polypeptides or mimeotopes that block the binding of maternal antibodies to one, two or all biomarkers selected from guanine deaminase (GDA), dihydropyrimidinase-like protein 2 (DPYSL2) and stress-induced phosphoprotein 1 (STIP1) is administered. In some embodiments, polypeptides or mimeotopes that block the binding of maternal antibodies to one or both of lactate dehydrogenase (LDH) and dihydropyrimidinase-like protein 2 (DPYSL2) is administered. In some embodiments, polypeptides or mimeotopes that block the binding of maternal antibodies to one or both of guanine deaminase (GDA) and dihydropyrimidinase-like protein 2 (DPYSL2) is administered. In some embodiments, polypeptides or mimeotopes that block the binding of maternal antibodies to dihydropyrimidinase-like protein 2 (DPYSL2) is administered.

The administered anti-biomarker antibody blocking agents, polypeptides or small molecules may contain modifications to reduce or minimize their immunogenicity. Modifications to amino acids in the biomarker polypeptides and antigenic fragments thereof or biomarker mimeotopes include, but are not limited to, an amide moiety or a pyroglutamyl residue or the addition of polyethylene glycol chains (PEGylation). These modifications may contribute to decreasing the propensity to form β-sheet conformation or may contribute to peptide stability, solubility and decreased immunogenicity. A more stable, soluble and less immunogenic peptide is desirable. Many peptides modified at the C-terminus with a $CONH_2$ (amide) group appear to be resistant to attack by carboxypeptidases and many peptides having a pyroglutamyl residue at the N-terminus are more resistant to attack by broad specificity aminopeptidases. PEGylated peptides have been shown to have increased plasma half-lives and decreased immunogenicity as compared with non-modified peptides. Furthermore, sequence analysis of the blocking agents will allow the minimalization of known T-cell epitopes through conservative modifications. Also included as peptides of the present invention are cyclic peptides that are resistant to attack by both carboxypeptidases and aminopeptidases. Additionally, oral administration of the blocking agent may aid in minimizing immunogenicity.

In some embodiments, the prevention and/or treatment methods include the step of first determining the presence or increased presence of antibodies that bind to the one or more biomarkers in the mother or potential mother, as described herein. A woman who tests positive or at a level above the threshold level for the presence of anti-biomarker antibodies is a candidate to receive an agent(s) that block the binding of maternal anti-biomarker antibodies to the one or more target biomarkers. A woman who tests negative or at a level below the threshold level for the presence of anti-biomarker antibodies need not receive an agent(s) that blocks the binding of maternal anti-biomarker antibodies to the one or more target biomarkers.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein. Generally, an efficacious or effective amount of one or more anti-biomarker antibody blocking agents is determined by first administering a low dose or small amount of an anti-biomarker antibody blocking agents and then incrementally increasing the administered dose or dosages, and/or adding a second anti-biomarker antibody blocking agent(s) as needed, until a desired effect of, e.g., eliminating or reducing the presence of unbound or free anti-biomarker antibodies below a predetermined threshold level, is observed in the treated subject, with minimal or no toxic or undesirable side effects. Applicable methods for determining an appropriate dose and dosing schedule for administration of a pharmaceutical composition of the present invention is described, for example, in Goodman and Gilman's *The Pharmacological Basis of Therapeutics,* 11th Ed., Brunton, et al., Eds., McGraw-Hill (2006), and in *Remington: The Science and Practice of Pharmacy,* 21$^{st}$ Ed., University of the Sciences in Philadelphia (USIP), 2005, Lippincott, Williams and Wilkins, both of which are hereby incorporated herein by reference.

Dosage amount and interval can be adjusted individually to provide plasma or tissue levels of the anti-biomarker antibody blocking agent(s) sufficient to maintain a therapeutic effect. Single or multiple administrations of the compositions comprising an effective amount of one or more anti-biomarker antibody blocking agents can be carried out with does levels and pattern selected by the treating physician. The dose and administration schedule can be determined and adjusted, e.g., based on the levels of anti-biomarker antibodies in the mother or potential mother, which can be monitored throughout the course of treatment according to methods commonly practiced by clinicians or those described herein. In some embodiments, therapeutic levels will be achieved by administering single daily doses. In other embodiments, the dosing schedule can include multiple daily dose schedules. In still other embodiments, dosing every other day, semi-weekly, or weekly are included in the invention.

For example, the anti-biomarker antibody blocking agent(s) can be administered monthly, bi-weekly, weekly or daily, as needed. In some embodiments, the levels of anti-biomarker antibodies in the mother are monitored and the blocking agent(s) are administered if anti-biomarker antibodies are present or are present at levels above a predetermined threshold level. The anti-biomarker antibody blocking agent(s) can be administered for a time period of about 1, 2, 3, 4, 5, 10, 12, 15, 20, 24, 30, 32, 36 weeks, or longer or shorter, as appropriate. For example, administration of the anti-biomarker antibody blocking agent(s) can be discontinued if the level of anti-biomarker antibodies falls below the predetermined threshold level. The anti-biomarker antibody blocking agent(s) can be administered for the full duration of a pregnancy, or during one or more of the first, second or third trimesters of pregnancy. Administration can begin before conception and can continue after birth, for example, while the mother is breastfeeding the child.

In embodiments where the blocking agent(s) are a polypeptide, typical dosages can range from about 0.1 μg/kg body weight up to and including about 1 gm/kg body weight, for example, between about 1 μg/kg body weight to about 500 mg/kg body weight. In some embodiments, the dose of polypeptide is about 1, 2, 3, 4, 5, 10, 20, 30, 40, 50, 60, 70, 80, 90, or 100 mg/kg body weight.

In embodiments were the agent(s) are a small organic compound, typical dosages can range from about 0.1 μg/kg body weight up to and including about 1 gm/kg body weight, for example, between about 1 μg/kg body weight to about 500 mg/kg body weight. In some embodiments, the dose of small organic compound is about 0.1, 1, 2, 3, 4, 5, 10, 20, 30, 40, 50, 60, 70, 80, 90, or 100 mg/kg body weight.

The exact dose will depend on a variety of factors as discussed supra, including the particular inhibitor, severity of the disease, and route of administration. Determining the exact therapeutically effective dose can be determined by a clinician without undue experimentation and can include any dose included within the ranges disclosed above.

The anti-biomarker antibody blocking agent(s) are administered by a route of administration such that the agent(s) bind to the anti-biomarker antibody and prevents the binding of the antibody to endogenous biomarkers associated with risk of developing ASD and that immune responses to the agent are minimized. Usually the agent(s) are administered systemically. In some embodiments, the agent(s) are administered parenterally, e.g., intravenously or intra-amniotically (i.e., directly into the amniotic sac). Additionally the anti-biomarker blocking antibody may be administered orally.

The compounds can be formulated for parenteral administration by injection, e.g., by bolus injection or continuous infusion. For injection, an anti-biomarker antibody blocking agent(s) can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, a combination of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the anti-biomarker antibody blocking agent(s) in water-soluble form. Additionally, suspensions of the anti-biomarker antibody blocking agent(s) can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Treatment with the anti-biomarker antibody blocking agent(s) is considered efficacious if the levels or titer of anti-biomarker antibodies that actively bind the one or more biomarkers are reduced or eliminated in a biological sample from an individual after receiving one or more administrations of the blocking agent, in comparison to before administration of the blocking agent. For example, a reduction of anti-biomarker antibody antibodies that actively bind the one or more target biomarkers in a sample of at least about 10%, 25%, 50%, 75% or 100% after one or more administrations of the blocker indicates that administration of the blocking agent was efficacious. Where a threshold level has been established, treatment with the anti-biomarker antibody blocking agent(s) is considered efficacious if the levels or titer of anti-biomarker antibodies that actively bind the one or more biomarkers are reduced to below the threshold level. Anti-biomarker antibodies that actively bind the one or more biomarkers can be measured using any method known in the art, including those described herein.

In some embodiments, the anti-biomarker antibody blocking agent(s) are co-administered with another immunosuppressive therapy. The co-administered immunosuppressive therapy can be antigen specific (e.g., immunosuppressive DNA vaccination) or antigen non-specific (e.g., glucocorticoids, antibodies against CD20, CTLA-4, LFA-1). In some embodiments, the anti-biomarker antibody blocking agent is co-administered with an anti-CD20 antibody, useful in selectively depleting B-cell populations. Anti-CD20 antibodies clinically useful in depleting B-cells are available, including e.g., Rituximab, ocrelizumab and ofatumumab.

In a further aspect, the invention provides methods of preventing or reducing the risk of a fetus developing an ASD comprising administering to the mother of the fetus an agent that blocks the binding of maternal antibodies to one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase, whereby blocking the binding to the one or more fetal proteins of the maternal antibodies prevents or reduces the risk of the fetus developing an ASD. The blocking of the binding of maternal antibodies against one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase can be performed in conjunction with or independently from the blocking of the binding of maternal antibodies against the one or more biomarkers. Further embodiments of the blocking methods are as described herein.

5. Methods of Reducing Risk of ASD by Immunosuppressive DNA Vaccination

In an alternative embodiment, one or more polynucleotides encoding a biomarker polypeptide, antigenic fragments thereof or mimeotopes thereof, are administered to effect suppressive vaccination. The polynucleotide can be expressed from a vector, e.g., a plasmid vector, that has a low number of CG dinucleotides in order to reduce or minimize immunostimulatory activity. Immunosuppressive vaccination to counteract an autoimmune response has been described, e.g., in U.S. Pat. Nos. 7,030,098 and 7,544,669.

The polynucleotide can encode a biomarker polypeptide or an antigenic fragment thereof. For example, polynucleotides encoding partial length fragments of the biomarker polypeptides that are at least 10 amino acids in length and which are bound by anti-biomarker antibodies are administered. In some embodiments, polynucleotides encoding partial length fragments of the biomarker polypeptides that are at least about 50%, 60%, 70%, 80%, 90%, 95% of the full length of the biomarker polypeptide are administered. In some embodiments, polynucleotides encoding partial length fragments of the one or more biomarkers are about 10, 25, 50, 100, 150, 200, 250 or 300 amino acids in length are administered. The partial length fragments can have the N-terminus or the C-terminus of biomarker polypeptide removed, or part of both of the N-terminus and the C-terminus removed. Polynucleotides encoding partial length fragments of one or more biomarker polypeptides that bound by anti-biomarker antibodies find use.

In some embodiments, a polynucleotide encoding one or more of an LDH-A and/or an LDH-B is administered. In some embodiments, a polynucleotide encoding one or more isozymes of an LDH-1, LDH-2, LDH-3, LDH-4 and/or LDH-5 are administered. In some embodiments, a polynucleotide encoding an LDH polypeptide or antigenic fragment thereof having at least about 90%, 93%, 95%, 97%, 99% or 100% sequence identity with an LDH polypeptide as described herein, e.g., with an amino acid sequence of GenBank Accession No. NP_001128711, NP_005557.1, AAP36496.1, BAD96798.1, or NP_002291.1 is administered.

In some embodiments, the administered polynucleotide encodes a biomarker polypeptide or antigenic fragment thereof that has at least about 90%, 93%, 95%, 97%, 99% or 100% sequence identity with a biomarker polypeptide as described herein, e.g., with a LDHA amino acid sequence of GenBank Accession No. AAP36496.1; BAD96798.1; NP_005557.1 (isoform 1); NP_001128711.1 (isoform 2); NP_001158886.1 (isoform 3); NP_001158887.1 (isoform 4); or NP_001158888.1 (isoform 5); with a LDHB. amino acid sequence of GenBank Accession No. NP_002291.1 (variant 1); or NP_001167568.1 (variant 2); with a CRMP1 amino acid sequence of GenBank Accession No. NP_001014809.1 (isoform 1) or NP_001304.1 (isoform 2); with a STIP1 amino acid sequence of GenBank Accession No. NP_006810.1; with a GDA amino acid sequence of GenBank Accession No. NP_004284.1; with a DPYSL2 amino acid sequence of GenBank Accession No. NP_001377.1 or BAD92432; with a CAPZA2 amino acid sequence of GenBank Accession No. NP_006127.1; with an YBX1 amino acid sequence of GenBank Accession No. NP_004550.2; with an EEF1A1 amino acid sequence of GenBank Accession No. NP_001393.1; with MAPT amino acid sequence of GenBank Accession No. NP_058519.3 (isoform 1); NP_005901.2 (isoform 2); NP_058518.1 (isoform 3); NP_058525.1 (isoform 4); NP_001116539.1 (isoform 5); or NP_001116538.2 (isoform 6); with a DNM1L amino acid sequence of GenBank Accession No. NP_036192.2 (isoform 1); NP_036193.2 (isoform 2); NP_005681.2 (isoform 3); with a NEFL amino acid sequence of GenBank Accession No. NP_006149.2; with a RDX amino acid sequence of GenBank Accession No. NP_002897.1; with a MSN amino acid sequence of GenBank Accession No. NP_002435.1; or with an EZR amino acid sequence of GenBank Accession No. NP_003370.2 (isoform 1) or NP_001104547.1 (isoform 2).

In some embodiments, the polynucleotide encodes a biomarker mimeotope that binds to anti-biomarker antibodies. The biomarker mimeotope can be derived from a known antigenic epitope of the one or more biomarkers, with one or more amino acids substituted, deleted or added. The biomarker mimeotope can be designed or identified de novo, by screening a peptide library for mimeotopes that bind to antibodies against the one or more biomarkers.

The polynucleotide is administered via a route to effect suppressive vaccination, e.g., intramuscularly, intravenously, subcutaneously or intranasally. Usually, the polynucleotide is administered intramuscularly.

The mother or potential mother is first tested to determine the presence of anti-biomarker antibodies or the presence of anti-biomarker antibodies above a predetermined threshold level. A suppressive immunization regimen can then be commenced. The immunosuppressive vaccination regimen can be started before, during or after pregnancy, as appropriate.

A vector with minimized or eliminated CpGs and encoding the one or more of the biomarker polypeptides, the antigenic fragment thereof or the biomarker mimeotope can be administered one, two, three, four, or more times as needed to selectively suppress the mother's immune response against the one or more biomarkers. The low CpG vector can be delivered, e.g., monthly for 6-12 months, and then every 3-12 months as a maintenance dose. Alternative treatment regimens may be developed and may range from daily, to weekly, to bi-weekly, to every other month, to yearly, to a one-time administration depending upon the severity of the disease, the age of the patient, the one or more biomarker polypeptides or antigenic fragments being administered and such other factors as would be considered by the ordinary treating physician. A suppressive immunization course may start out with more frequent administrations and then continue with follow-up boosters.

Therapeutically effective amounts of the low CpG vector are in the range of about 0.001 micrograms to about 1 gram. A preferred therapeutic amount of vector is in the range of about 10 micrograms to about 5 milligrams. A most preferred therapeutic amount of self-vector is in the range of about 0.025 mg to 5 mg.

Immunosuppressive vaccination is considered efficacious if the levels or titer of anti-biomarker antibodies that actively bind the one or more biomarkers are reduced or eliminated in a biological sample from an individual after receiving one or more administrations of the vector encoding the one or more biomarker polypeptides or antigenic fragments, in comparison to before administration of the vector. For example, a reduction of anti-biomarker antibodies that actively bind the one or more biomarkers in a sample of at least about 10%, 25%, 50%, 75% or 100% after one or more administrations of the vector encoding the biomarker polypeptide or antigenic fragment indicates that administration of the vector was efficacious. Where a threshold level has been established, treatment with the vector comprising a polynucleotide encoding the one or more biomarker polypeptides or antigenic fragments is considered efficacious if the levels or titer of anti-biomarker antibodies that actively bind the one or more biomarker polypeptides are reduced to below the threshold level. Anti-biomarker antibodies that actively bind the one or more biomarker polypeptides can be measured using any method known in the art, including those described herein.

In some embodiments, the low CpG vector contains a polynucleotide encoding one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase. The polynucleotide encoding the one or more fetal proteins can be administered concurrently with or independently of a polynucleotide encoding a biomarker polypeptide or an antigenic fragment thereof, as described herein. Further embodiments for administration of the polynucleotides encoding the fetal proteins are described herein.

6. Methods of Reducing Risk by Removing Anti-Biomarker Antibodies

The risk of the fetus or child developing an ASD can be reduced or eliminated by removing the maternal anti-biomarker antibodies from a biological fluid of the mother ex vivo, and then returning the biological fluid, with reduced or eliminated levels of anti-biomarker antibodies, to the mother.

The ex vivo removal of anti-biomarker antibodies can be carried out on a woman before, during or after pregnancy. In some embodiments, the anti-biomarker antibodies are removed from the biological fluid one, two, three, four or more times, as appropriate, at any time during the course of pregnancy. For example, the anti-biomarker antibodies can be removed in one or more of the first, second and/or third trimesters of pregnancy. In some embodiments, the anti-biomarker antibodies are removed from a woman carrying a fetus whose brain has begun to develop, e.g., after about 12 weeks of gestation. In some embodiments, the anti-biomarker antibodies are removed one or more times post-partum, e.g., in the first four weeks after birth and/or while the mother is breastfeeding the child. In some embodiments, the anti-biomarker antibodies are removed one or more times before pregnancy, for example, in a woman who has tested positive for anti-biomarker antibodies and who is trying to become pregnant.

The process of ex vivo anti-biomarker antibody removal can be performed one, two, three, four, or more times, as needed to eliminate or reduce anti-biomarker antibodies from the mother. Ex vivo removal of the anti-biomarker antibodies can be performed daily, weekly, bi-weekly, monthly, bi-monthly, as appropriate. In some embodiments, the levels of anti-biomarker antibodies in the mother are monitored and ex vivo anti-biomarker antibody removal performed if the presence of anti-biomarker antibodies are above a predetermined threshold level. Ex vivo anti-biomarker antibody removal can be carried out over a time period of a 1, 2, 3, 4, 5, 10, 12, 15, 20, 25, 35, 36 weeks, or longer or shorter, as appropriate. For example, ex vivo removal of anti-biomarker antibodies can be discontinued if the level of anti-biomarker antibodies falls below the predetermined threshold level. Ex vivo anti-biomarker antibody removal can be conducted for the full duration of a pregnancy, or during one or more of the first, second or third trimesters of pregnancy. Anti-biomarker antibody removal can begin before conception and can continue after birth, for example, while the mother is breastfeeding the child.

The biological fluid will contain maternal anti-biomarker antibodies. Usually, the biological fluid is blood, serum, plasma or milk. In some embodiments, the biological fluid is amniotic fluid.

The maternal biological fluid containing anti-biomarker antibodies is contacted with one or more of the biomarker polypeptides or an antigenic fragments thereof. The one or more biomarker polypeptides or antigenic fragments can be purified or substantially purified from a natural source, or recombinantly or synthetically produced, as discussed above. For example, partial length fragments of the one or more biomarker polypeptides that are at least 10 amino acids in length and which are bound by anti-biomarker antibodies can be contacted with the biological fluid. In some embodiments, the partial length fragments of the one or more biomarker polypeptides that are at least about 50%, 60%, 70%, 80%, 90%, 95% of the full length of the biomarker polypeptides can be contacted with the biological fluid. In some embodiments, the partial length fragments of the one or more biomarker polypeptides are about 10, 25, 50, 100, 150, 200, 250 or 300 amino acids in length. The partial length fragments can have the N-terminus or the C-terminus of the biomarker polypeptide removed, or part of both of the N-terminus and the C-terminus removed. Partial length fragments of the one or more biomarker polypeptides that find use are bound by anti-biomarker antibodies.

In some embodiments, the biological fluid is contacted with one or more of an LDH-A and/or an LDH-B. In some embodiments, the biological fluid is contacted with one or more isozymes of an LDH-1, LDH-2, LDH-3, LDH-4 and/or LDH-5. In some embodiments, the LDH polypeptide or antigenic fragment thereof has at least about 90%, 93%, 95%, 97%, 99% or 100% sequence identity with an LDH polypeptide as described herein, e.g., with an amino acid sequence of GenBank Accession No. NP_001128711, NP_005557.1, AAP36496.1, BAD96798.1, or NP_002291.1.

In some embodiments, the biological fluid is contacted with one or more biomarker polypeptides or antigenic fragments thereof having at least about 90%, 93%, 95%, 97%, 99% or 100% sequence identity with a biomarker polypeptide as described herein, e.g., with a LDHA amino acid sequence of GenBank Accession No. AAP36496.1; BAD96798.1; NP_005557.1 (isoform 1); NP_001128711.1 (isoform 2); NP_001158886.1 (isoform 3); NP_001158887.1 (isoform 4); or NP_001158888.1 (isoform 5); with a LDHB. amino acid sequence of GenBank Accession No. NP_002291.1 (variant 1); or NP_001167568.1 (variant 2); with a CRMP1 amino acid sequence of GenBank Accession No. NP_001014809.1 (isoform 1) or NP_001304.1 (isoform 2); with a STIP1 amino acid sequence of GenBank Accession No. NP_006810.1; with a GDA amino acid sequence of GenBank Accession No. NP_004284.1; with a DPYSL2 amino acid sequence of GenBank Accession No. NP_001377.1 or BAD92432; with a CAPZA2 amino acid sequence of GenBank Accession No. NP_006127.1; with an YBX1 amino acid sequence of GenBank Accession No. NP_004550.2; with an EEF1A1 amino acid sequence of GenBank Accession No. NP_001393.1; with MAPT amino acid sequence of GenBank Accession No. NP_058519.3 (isoform 1); NP_005901.2 (isoform 2); NP_058518.1 (isoform 3); NP_058525.1 (isoform 4); NP_001116539.1 (isoform 5); or NP_001116538.2 (isoform 6); with a DNM1L amino acid sequence of GenBank Accession No. NP_036192.2 (isoform 1); NP_036193.2 (isoform 2); NP_005681.2 (isoform 3); with a NEFL amino acid sequence of GenBank Accession No. NP_006149.2; with a RDX amino acid sequence of GenBank Accession No. NP_002897.1; with a MSN amino acid sequence of GenBank Accession No. NP_002435.1; or with an EZR amino acid sequence of GenBank Accession No. NP_003370.2 (isoform 1) or NP_001104547.1 (isoform 2).

In some embodiments, the anti-biomarker antibody removal agent is a mimeotope of a biomarker. The biomarker mimeotope can be derived from a known antigenic epitope of the target biomarker, with one or more amino acids substituted, deleted or added. The biomarker mimeotope can be designed or identified de novo, by screening a peptide library for mimeotopes that bind to antibodies against the one or more biomarkers.

In some embodiments, biological fluid from the mother or potential mother is contacted with a biomarker polypeptide or antigenic fragment thereof, or biomarker mimeotope immobilized on a solid support. The solid support, can be, for example, a bead, a column, a filter. The immobilization can be via covalent or non-covalent binding. In some embodiments, the immobilization is through a capture antibody that specifically binds to the target biomarker. The biomarker polypeptide or antigenic fragments thereof, or the biomarker mimeotope attached to the solid support is a stationary phase that captures the anti-biomarker antibodies in the biological fluid allowing the biological fluid with reduced or eliminated levels of anti-biomarker antibodies to be separated from the solid support, i.e., as the mobile phase, and returned to the mother or potential mother.

In some embodiments, the biological fluid that is processed ex vivo is plasma, and the anti-biomarker antibodies are removed by plasmapheresis, a process well known in the art. The plasma is contacted with a solid support with immobilized one or more biomarker polypeptides or antigenic fragments thereof, or immobilized biomarker mimeotopes. Anti-biomarker antibodies in the plasma bind to the immobilized biomarker polypeptides or antigenic fragments thereof, or immobilized biomarker mimeotopes. Plasma with reduced or eliminated levels of anti-biomarker antibodies is then returned to the mother or potential mother.

In a related aspect, the invention provides methods of preventing or reducing the risk of a fetus developing an ASD comprising removing antibodies that specifically bind to one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase from the mother of the fetus. The removal of maternal antibodies against one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase can be performed in conjunction with or independently from the removal of the binding of maternal antibodies against the one or more biomarkers. Further methods for the removal of the maternal antibodies are as described herein.

7. Kits

The invention also provides kits for the diagnosis or prognosticating of whether a fetus or child is at an increased risk of developing an ASD. Relatedly, the kits also find use for the diagnosis or prognosticating of whether a mother or potential mother is at an increased risk of bearing a child who will develop an ASD. In some embodiments, the kits comprise a solid support comprising one or more subunits or one or more isotypes of the one or more biomarkers, or antigenic fragments thereof (e.g., a solid support comprising 1, 2, 3, 4, 5, 6, 7, 8, 9, 10, 11, 12, 13, or more biomarkers selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)).

In some embodiments, the solid support comprises one, two, three or all biomarkers selected from lactate dehydrogenase (LDH), guanine deaminase (GDA), collapsin response mediator protein 1 (CRMP1) and stress-induced phosphoprotein 1 (STIP1). In some embodiments, the solid support comprises one, two or all biomarkers selected from lactate dehydrogenase (LDH), collapsin response mediator protein 1 (CRMP1) and stress-induced phosphoprotein 1 (STIP1). In some embodiments, the solid support comprises one, two or all biomarkers selected from guanine deaminase (GDA), collapsin response mediator protein 1 (CRMP1) and stress-induced phosphoprotein 1 (STIP1). In some embodiments, the solid support comprises one or both of lactate dehydrogenase (LDH) and collapsin response mediator protein 1 (CRMP1). In some embodiments, the solid support comprises one or both of guanine deaminase (GDA) and collapsin response mediator protein 1 (CRMP1). In some embodiments, the solid support comprises one or both of lactate dehydrogenase (LDH) and stress-induced phosphoprotein 1 (STIP1). In some embodiments, the solid support comprises one or both of guanine deaminase (GDA) and stress-induced phosphoprotein 1 (STIP1). In some embodiments, the solid support comprises lactate dehydrogenase (LDH). In some embodiments, the solid support comprises guanine deaminase (GDA). In some embodiments, the solid support comprises collapsin response mediator protein 1 (CRMP1). In some embodiments, the solid support comprises stress-induced phosphoprotein 1 (STIP1).

In some embodiments, the solid support comprises one, two, three or all biomarkers selected from lactate dehydrogenase (LDH), guanine deaminase (GDA), dihydropyrimidinase-like protein 2 (DPYSL2) and stress-induced phosphoprotein 1 (STIP1). In some embodiments, the solid support comprises one, two or all biomarkers selected from lactate dehydrogenase (LDH), dihydropyrimidinase-like protein 2 (DPYSL2) and stress-induced phosphoprotein 1 (STIP1). In some embodiments, the solid support comprises one, two or all biomarkers selected from guanine deaminase (GDA), dihydropyrimidinase-like protein 2 (DPYSL2) and stress-induced phosphoprotein 1 (STIP1). In some embodiments, the solid support comprises one or both of lactate dehydrogenase (LDH) and dihydropyrimidinase-like protein 2 (DPYSL2). In some embodiments, the solid support comprises one or both of guanine deaminase (GDA) and dihydropyrimidinase-like protein 2 (DPYSL2). In some embodiments, the solid support comprises dihydropyrimidinase-like protein 2 (DPYSL2).

The solid support, can be, for example, a multiwell plate, an ELISA plate, a microarray chip, a bead, a porous strip, a nitrocellulose filter. The immobilization can be via covalent or non-covalent binding. In some embodiments, the immobilization is through a capture antibody that specifically binds to the one or more biomarkers. The solid supports in the kits are provided prepared with one or more immobilized biomarker polypeptides, antigenic fragments thereof, or biomarker mimeotopes.

In some embodiments, the one or more biomarker polypeptides or an antigenic fragments thereof is immobilized on the solid support. The biomarker polypeptide or antigenic fragment can be purified or substantially purified from a natural source, or recombinantly or synthetically produced, as discussed above. For example, one or more partial length fragments of the one or more biomarkers can be immobilized that are at least 10 amino acids in length and which are bound by anti-biomarker antibodies. In some embodiments, the partial length fragments of the one or more biomarkers that are immobilized are at least about 50%, 60%, 70%, 80%, 90%, 95% of the full length of the biomarker polypeptide. In some embodiments, the partial length fragments of the one or more biomarker polypeptides are about 10, 25, 50, 100, 150, 200, 250 or 300 amino acids in length. The partial length fragments can have the N-terminus or the C-terminus of the biomarker removed, or part of both of the N-terminus and the C-terminus removed. Partial length fragments of the one or more biomarkers that find use are bound by anti-biomarker antibodies.

In some embodiments, one or more of an LDH-A and/or an LDH-B is immobilized on the solid support. In some embodiments, one or more isozymes of an LDH-1, LDH-2, LDH-3, LDH-4 and/or LDH-5 are immobilized on the solid support. In some embodiments, the LDH polypeptide or antigenic fragment thereof has at least about 90%, 93%, 95%, 97%, 99% or 100% sequence identity with an LDH polypeptide as described herein, e.g., with an amino acid sequence of GenBank Accession No. NP_001128711, NP_005557.1, AAP36496.1, BAD96798.1, or NP_002291.1.

In some embodiments, the solid support comprises one or more biomarker polypeptides or antigenic fragments thereof having at least about 90%, 93%, 95%, 97%, 99% or 100% sequence identity with a biomarker polypeptide as described herein, e.g., with a LDHA amino acid sequence of GenBank Accession No. AAP36496.1; BAD96798.1; NP_005557.1 (isoform 1); NP_001128711.1 (isoform 2); NP_001158886.1 (isoform 3); NP_001158887.1 (isoform 4); or NP_001158888.1 (isoform 5); with a LDHB. amino acid sequence of GenBank Accession No. NP_002291.1 (variant 1); or NP_001167568.1 (variant 2); with a CRMP1 amino acid sequence of GenBank Accession No. NP_001014809.1 (isoform 1) or NP_001304.1 (isoform 2); with a STIP1 amino acid sequence of GenBank Accession No. NP_006810.1; with a GDA amino acid sequence of GenBank Accession No. NP_004284.1; with a DPYSL2 amino acid sequence of GenBank Accession No. NP_001377.1 or BAD92432; with a CAPZA2 amino acid sequence of GenBank Accession No. NP_006127.1; with an YBX1 amino acid sequence of GenBank Accession No. NP_004550.2; with an EEF1A1 amino acid sequence of GenBank Accession No. NP_001393.1; with MAPT amino acid sequence of GenBank Accession No. NP_058519.3 (isoform 1); NP_005901.2 (isoform 2); NP_058518.1 (isoform 3); NP_058525.1 (isoform 4); NP_001116539.1 (isoform 5); or NP_001116538.2 (isoform 6); with a DNM1L amino acid sequence of GenBank Accession No. NP_036192.2 (isoform 1); NP_036193.2 (isoform 2); NP_005681.2 (isoform 3); with a NEFL amino acid sequence of GenBank Accession No. NP_006149.2; with a RDX amino acid sequence of GenBank Accession No. NP_002897.1; with a MSN amino acid sequence of GenBank Accession No. NP_002435.1; or with an EZR amino acid sequence of GenBank Accession No. NP_003370.2 (isoform 1) or NP_001104547.1 (isoform 2).

In some embodiments, the solid support comprises one or more biomarker mimeotopes that bind to an anti-biomarker antibody. The biomarker mimeotope can be derived from a known antigenic epitope of the biomarker, with one or more amino acids substituted, deleted or added. The biomarker mimeotope can be designed or identified de novo, by screening a peptide library for mimeotopes that bind to antibodies against the biomarker.

In some embodiments, the kits also comprise labeled secondary antibodies used to detect antibodies or autoantibodies in a sample that have bound to one or more biomarker polypeptides, antigenic fragments thereof or biomarker mimeotopes. The secondary antibodies bind to the constant or "C" regions of different classes or isotypes of immunoglobulins—IgM, IgD, IgG, IgA, and IgE. Usually, a secondary antibody against an IgG constant region is included in the kits, for example, a secondary antibodies against one of the IgG subclasses, for example, IgG1, IgG2, IgG3, and IgG4. Secondary antibodies can be labeled with any directly or indirectly detectable moiety, including a fluorophore (i.e., fluoroscein, phycoerythrin, quantum dot, Luminex bead, fluorescent bead), an enzyme (i.e., peroxidase, alkaline phosphatase), a radioisotope (i.e., $^{3}H$, $^{32}P$, $^{125}I$) or a chemiluminescent moiety. Labeling signals can be amplified using a complex of biotin and a biotin binding moiety (i.e., avidin, streptavidin, neutravidin). Fluorescently labeled anti-human IgG antibodies are commercially available from Molecular Probes, Eugene, Oreg. Enzyme-labeled anti-human IgG antibodies are commercially available from Sigma-Aldrich, St. Louis, Mo. and Chemicon, Temecula, Calif.

The kits further comprise instructions for contacting the solid supports with a biological sample from a mother or potential mother, and for correlating the presence of maternal anti-biomarker antibodies or levels of maternal anti-biomarker antibodies above a threshold level with the increased probability of the fetus or child to develop an ASD.

In some embodiments, the kits also contain negative and positive control samples for detection of anti-biomarker antibodies. In some embodiments, the kits contain samples for the preparation of a titrated curve of anti-biomarker antibodies in a sample, to assist in the evaluation of quantified levels of anti-biomarker antibodies in a test biological sample.

The kits find use for providing a diagnosis or prognosis to any women of childbearing age. A diagnosis or prognosis can be determined before, during or after pregnancy. As discussed above, detection of anti-biomarker antibodies can be made in one or more of the first, second and/or third trimesters of pregnancy. In some embodiments, detection of anti-biomarker antibodies is performed on a biological sample from a woman carrying a fetus whose brain has begun to develop, e.g., after about 12 weeks of gestation. In some embodiments, the presence or absence of anti-biomarker antibodies or the quantified levels of anti-biomarker antibodies are evaluated one or more times post-partum, e.g., in the first four weeks after birth and/or while the mother is breastfeeding the child. In some embodiments, the presence or absence of anti-biomarker antibodies or the quantified levels of anti-biomarker antibodies are evaluated one or more times before pregnancy or in any women who is not pregnant.

In some embodiments, the kits contain a solid support with one or more immobilized proteins selected from the group consisting of one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase, including antigenic fragments or mimeotopes thereof. The support may also have an immobilized biomarker polypeptide, antigenic fragment thereof, or mimeotope thereof. Instructions for correlating the presence of maternal antibodies against the one or more fetal proteins, as well as positive and negative control samples, may also be included in the kits. Further embodiments of the kits are as described herein.

8. Screening for Blocking Agents

Identification of agents that inhibit anti-biomarker antibodies from binding to the target biomarker can be assessed using a variety of in vitro assays, including those described herein. Such assays can be used to test for inhibitors of anti-biomarker antibodies (e.g., against 1, 2, 3, 4, 5, 6, 7, 8, 9, 10, 11, 12, 13, or more, biomarkers selected from lactate dehydrogenase (LDH), guanine deaminase (GDA), collapsin response mediator protein 1 (CRMP1), stress-induced phosphoprotein 1 (STIP1), alpha subunit of the barbed-end actin binding protein Cap Z (CAPZA2), Y Box Binding Protein 1 (YBX1), eukaryotic translation and elongation factor 1A1 (EEF1A1), microtubule-associated protein Tau (MAPT), dihydropyrimidinase-like protein 2 (DPYSL2), dynamin 1-like protein (DNM1L), radixin (RDX), moesin (MSN), and ezrin (EZR)), and consequently agents that find use to prevent, reduce or inhibit the development of an ASD.

In some embodiments, the screening assays employ a biomarker antigen, e.g., an biomarker polypeptide or an antigenic fragment thereof. The biomarker polypeptide or antigenic fragment can be purified or substantially purified from a natural source, or recombinantly or synthetically produced, as discussed above. For example, one or more partial length fragments of the one or more biomarkers that are at least 10 amino acids in length and which are bound by anti-biomarker antibodies are used. In some embodiments, partial length fragments of the one or more biomarkers of at least about 50%, 60%, 70%, 80%, 90%, 95% of the full length of the biomarker polypeptide are used. In some embodiments, the partial length fragments of the one or more biomarker polypeptides are about 10, 25, 50, 100, 150, 200, 250 or 300 amino acids in length. The partial length fragments can have the N-terminus or the C-terminus of the biomarker polypeptide removed, or part of both of the N-terminus and the C-terminus removed. Partial length fragments of the biomarker polypeptides that find use are bound by anti-biomarker antibodies.

In some embodiments, one or more of an LDH-A and/or an LDH-B are used. In some embodiments, one or more isozymes of an LDH-1, LDH-2, LDH-3, LDH-4 and/or LDH-5 are used. In some embodiments, the LDH polypeptide or antigenic fragment thereof has at least about 90%, 93%, 95%, 97%, 99% or 100% sequence identity with an LDH polypeptide as described herein, e.g., with an amino acid sequence of GenBank Accession No. NP_001128711, NP_005557.1, AAP36496.1, BAD96798.1, or NP_002291.1. The LDH antigen can also be an LDH mimeotope.

In some embodiments, the screening assays employ one or more biomarker polypeptides or antigenic fragments thereof having at least about 90%, 93%, 95%, 97%, 99% or 100% sequence identity with a biomarker polypeptide as described herein, e.g., with a LDHA amino acid sequence of GenBank Accession No. AAP36496.1; BAD96798.1; NP_005557.1 (isoform 1); NP_001128711.1 (isoform 2); NP_001158886.1 (isoform 3); NP_001158887.1 (isoform 4); or NP_001158888.1 (isoform 5); with a LDHB. amino acid sequence of GenBank Accession No. NP_002291.1 (variant 1); or NP_001167568.1 (variant 2); with a CRMP1 amino acid sequence of GenBank Accession No. NP_001014809.1 (isoform 1) or NP_001304.1 (isoform 2); with a STIP1 amino acid sequence of GenBank Accession No. NP_006810.1; with a GDA amino acid sequence of GenBank Accession No. NP_004284.1; with a DPYSL2 amino acid sequence of GenBank Accession No. NP_001377.1 or BAD92432; with a CAPZA2 amino acid sequence of GenBank Accession No. NP_006127.1; with an YBX1 amino acid sequence of GenBank Accession No. NP_004550.2; with an EEF1A1 amino acid sequence of GenBank Accession No. NP_001393.1; with MAPT amino acid sequence of GenBank Accession No. NP_058519.3 (isoform 1); NP_005901.2 (isoform 2); NP_058518.1 (isoform 3); NP_058525.1 (isoform 4); NP_001116539.1 (isoform 5); or NP_001116538.2 (isoform 6); with a DNM1L amino acid sequence of GenBank Accession No. NP_036192.2 (isoform 1); NP_036193.2 (isoform 2); NP_005681.2 (isoform 3); with a NEFL amino acid sequence of GenBank Accession No. NP_006149.2; with a RDX amino acid sequence of GenBank Accession No. NP_002897.1; with a MSN amino acid sequence of GenBank Accession No. NP_002435.1; or with an EZR amino acid sequence of GenBank Accession No. NP_003370.2 (isoform 1) or NP_001104547.1 (isoform 2).

Assays to identify compounds that inhibit anti-biomarker antibodies binding to one or more of the biomarkers can be either solid state or soluble. Preferably, a biomarker polypeptide, antigenic fragment thereof or biomarker mimeotope is immobilized on a solid support, either covalently or non-covalently. The in vitro screening assays can be either non-competitive or competitive. Techniques for detecting binding of an antibody or pool of antibodies to an antigen are known in the art and include those employing an anti-biomarker antibody or a biomarker antigen (i.e., a polypeptide of the one or more biomarkers, an antigenic fragment thereof, a mimeotope thereof) containing a detectable label or region, and those involving the immunoprecipitation or "pull-down" of anti-biomarker antibodies that bind to the target biomarker. References for performing immunoassays are described above.

Numerous assay formats that can be employed include FACS analysis, scintillation proximity assays ("SPA"), and sandwich-type antibody assays. Also, membrane-coated solid supports (e.g., beads and array surfaces) find use in screening for compounds that inhibit the binding between an anti-biomarker antibody and the target biomarker. See, e.g., Baksh, et al., Nature (2004) 427:139; Winter and Groves, Anal Chem (2006) 78:17-80; Moura and Carmona-Ribeiro, Cell Biochem Biophys (2006) 44:446-52; and U.S. Pat. No. 6,228,326. Such membrane-coated surfaces find use in high throughput screening methods.

Techniques for performing a SPA are well known in the art. SPA can be performed using a bead or a plate coated with a scintillant fluid and a radiolabeled molecule. Proximity of the radiolabeled molecule to the scintillant fluid stimulates light emission. SPA can be used to measure binding of an anti-biomarker antibody to a target biomarker by, for example, joining an anti-biomarker antibody or biomarker polypeptide or antigenic fragment thereof to a SPA bead, radiolabeling the binding partner, i.e., the biomarker polypeptide or antigenic fragment thereof or the anti-biomarker antibody, respectively, and measuring the ability of a test compound to inhibit light production from the radiolabeled polypeptide.

In one embodiment, a solid-phase immunoassay, e.g., ELISA, electrochemiluminescence, is used to screen for inhibitors of anti-biomarker antibodies binding to one or more of the ASD biomarkers. In some solid phase immunoassays, beads or multiplate wells (e.g., 96-well, 384-well, 1536-well) can be coated directly or indirectly with at least one of anti-biomarker antibodies from a biological sample, a monoclonal anti-biomarker antibody, a biomarker polypeptide or antigenic fragments thereof or a biomarker mimeotope. The antibody can be an intact antibody or antibody fragments, e.g., an Fab or a single chain variable region. The antibody or antigen are directly coated onto the multiwell plate or indirectly coated through a capture antibody. The immobilized antibody or antigen is then exposed to a candidate blocking compound. In competition assays, a labeled (e.g., an enzyme, a radioisotope, a fluorophore, etc.) binding partner which was not immobilized, e.g., a biomarker antigen or an anti-biomarker antibody, is then used to detect whether the candidate blocking agent inhibited binding between the antibody and the antigen. In a non-competitive assay, the candidate blocking agent can be labeled and evaluated for direct binding to either an immobilized anti-biomarker antibody or an immobilized biomarker antigen.

In one embodiment, direct binding interactions between an anti-biomarker antibody and a biomarker antigen is measured using a FRET assay. FRET is a distance-dependent interaction between the electronic excited states of two dye molecules in which excitation is transferred from a donor molecule to an acceptor molecule without emission of a photon. The excitation transfer is distance dependent, and can be used to determine the proximity of two dye labeled macromolecules. For energy transfer to occur, donor and acceptor molecules must be in close proximity (typically 10-100 Å). Also, the absorption spectrum of the acceptor must overlap the fluorescence emission spectrum of the donor, so it is necessary to use compatible pairs of dyes for macromolecule labeling, for example, Cy3/Cy5 and Cy5/Cy5.5. In practice, interaction of pairs of proteins such as an anti-biomarker antibody and a biomarker antigen can be determined by individually labeling the anti-biomarker with a first dye in the compatible pair, and the biomarker antigen with a second dye in the compatible pair, and then FRET can be detected by the fluorescence emission of the acceptor or by quenching of donor fluorescence when the proteins are mixed in an assay. If labeled anti-biomarker antibody and biomarker antigen show a measurable FRET, this indicates a direct interaction between the anti-biomarker antibody and biomarker antigen. The FRET assay format can also be carried out with a labeled candidate blocker and either a labeled anti-biomarker antibody or a labeled biomarker antigen.

High Throughput Screening for Anti-Biomarker Antibody Inhibitors

The screening methods for blockers of anti-biomarker antibody binding to a biomarker antigen can be conveniently carried out using high-throughput methods.

In some embodiments, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Solid Phase and Soluble High Throughput Assays

In high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule that binds the tag (a tag binder) is fixed to a solid support, and the tagged molecule of interest (e.g., an anti-biomarker antibody or a biomarker antigen) is attached to the solid support by interaction of the tag and a tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Common linkers such as peptides, polyethers, and the like can also serve as tags, and include polypeptide sequences, such as poly Gly sequences of between about 5 and 200 amino acids (SEQ ID NO:2). Such flexible linkers are known to those of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, J. Am. Chem. Soc. 85:2149-2154 (1963) (describing solid phase synthesis of, e.g., peptides); Geysen et al., J. Immun. Meth. 102:259-274 (1987) (describing synthesis of solid phase components on pins); Frank and Doring, Tetrahedron 44:60316040 (1988) (describing synthesis of various peptide sequences on cellulose disks); Fodor et al., Science, 251:767-777 (1991); Sheldon et al., Clinical Chemistry 39(4):718-719 (1993); and Kozal et al., Nature Medicine 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the interaction of an anti-biomarker antibody and a biomarker antigen. Control reactions that measure interaction of an anti-biomarker antibody and a biomarker antigen, in the absence of a potential modulator, or in the presence of a known modulator, are optional, as the assays are highly uniform. Such optional control reactions however may be appropriate and increase the reliability of the assay.

Computer-Based Assays

Yet another assay for compounds that modulate the interaction of an anti-biomarker antibody and a biomarker antigen involves computer assisted drug design, in which a computer system is used to generate a three-dimensional structure of a biomarker polypeptide based on the structural information encoded by its amino acid sequence. The input amino acid sequence interacts directly and actively with a pre-established algorithm in a computer program to yield secondary, tertiary, and quaternary structural models of the protein. Similar analyses can be performed on the binding sites of an anti-biomarker antibody. The models of the protein structure are then examined to identify regions of the structure that have the ability to bind anti-biomarker antibodies, or a biomarker antigen, as appropriate. These regions are then used to identify polypeptides or other molecules that bind to an anti-biomarker antibody or a biomarker antigen. Suitable programs for structure analysis include Pyol Molecular Graphic Systems, published by Delano Scientific, Palo Alto, Calif.

In some embodiments, agents that block the binding of maternal antibodies to one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase are identified by the screening methods described herein. Screening for agents that block the binding of maternal antibodies to one or more fetal proteins selected from the group consisting of Guanine Nucleotide Binding Protein 1, Glyceraldehyde 3-Phosphate Dehydrogenase, F-Actin capping protein, alpha-2 subunit, Uracil DNA Glycosylase, and Glutamate Dehydrogenase can be performed concurrently with or independently from screening for agents that block the binding of maternal antibodies to one or more of the biomarkers described herein.

EXAMPLES

The following examples are offered to illustrate, but not to limit the claimed invention.

Example 1

Identification of Additional Fetal Brain Antigens

This example summarizes the identification of fetal brain antigens with apparent molecular weights of 37 kDa, 39 kDa and 73 kDa bound by maternal antibodies.

Materials and Methods

Study Subjects

Consenting mothers were enrolled through the Center for Children's Environmental Health (CCEH) as part of the ongoing CHARGE (Childhood Autism Risks from Genetics and Environment) study at the M.I.N.D. Institute at the University of California at Davis as described previously (Hertz-Picciotto, et al., *Environ Health Perspect*, (2006) 114(7): 1119-25). The CHARGE study population was sampled from three strata: children considered to have autism or autism spectrum disorders (ASD), children selected from the general population who were typically developing (TD), and children with developmental disabilities without autism (DD). Families were recruited for this study without bias for any medical or demographic factors. Diagnosis of all enrolled children was confirmed at the UC Davis M.I.N.D. Institute as previously described (Hansen, et al., *Ambul Pediatr*, (2008) 8(1): 25-31).

Sample Collection

Maternal blood was collected in yellow-top acid citrate dextrose tubes (BD Diagnostic, Franklin Lakes, N.J.). Plasma was separated from cells, coded, and aliquoted to minimize freeze/thaw cycles and stored at −80° C. until use.

Antigen Preparation

Fetal Rhesus macaque brain (152 days gestation) was acquired from the California National Primate Research Center and used to prepare a protein extract. Tissue was homogenized in a detergent buffer containing a phosphatase and protease inhibitor cocktail (Roche Complete) and subjected to sonication. Insoluble material was removed by centrifugation and a buffer exchange was performed to 50 mM Tris-HCl containing 1% LDS. Protein concentration was determined using the bicinchoninic acid (BCA) reaction (Pierce, Rockford, Ill.) and was adjusted to 4.5 mg/ml.

Western Blot

For initial screening of maternal plasma samples, 300 μg of prepared fetal Rhesus brain protein (FRB) was separated under reducing conditions in a prep well 4-12% gradient SDS-PAGE mini-gel (Invitrogen, Carlsbad, Calif.) and transferred electrophoretically to 0.2 μm pore-size nitrocellulose. MagicMark molecular weight marker (Invitrogen) was loaded in the single marker lane allowing chemiluminescent visualization of marker bands. Blots were stained with Ponceau S (MP Biomedicals, Solon, Ohio) to verify uniform protein loading, migration and transfer. The nitrocellulose membrane was then cut into 3 mm wide strips and probed with maternal plasma diluted 1:400. After washing, strips were incubated with 1:20,000 diluted HRP conjugated goat anti-human IgG (Invitrogen). The strips were then washed, incubated with SuperSignal West Chemilluminescent Substrate (Thermo Scientific) and aligned on a glass plate for imaging. Chemilluminescent images were acquired with a Fluor Chem 8900 imager using AlphaEaseFC software (Alpha Innotech, San Leandro, Calif.). Mothers found to react against FRB were subsequently used for antigen identification.

Prep Cell 100 mg of FRB was separated by molecular weight using a Prep Cell apparatus (Bio Rad, Hercules, Calif.). Briefly, FRB was electrophoresed through a 28 mm cylindrical 10% polyacrylamide gel for 17 hrs at 12 watts. A peristaltic pump attached to a chamber below the gel draws proteins which have migrated off of the gel to a fraction collector which begins collection when the dye front reaches the chamber. A total of 110 fractions were collected at 5 minute intervals at a flow rate of 0.75 ml/min. Fractions were concentrated to 5 mg/ml using Amicon Ultra-4 with Ultracel-10k membranes (Millipore, Co. Cork, Ireland) and assayed by Western blot to determine molecular weight and verify antigen reactivity (FIG. 1). Ponceau staining of Western blot membranes confirmed substantial enrichment for proteins by molecular weight, yielding fractions with approximately 5 kDa ranges which facilitated subsequent analysis. Fractions containing the 37 kDa, 39 kDa or 73 kDa proteins were selected for protein identification.

2-D Electrophoresis

Protein fractions derived from Prep Cell separation which were enriched for antigens recognized by maternal antibodies were separated by 2-D electrophoresis. 30 μg each of 37 kDa, 39 kDa or 73 kDa fractions were labeled with Cy2 (GE Life Sciences) and prepared for 2-D gel electrophoresis. All 2-D gels were performed in duplicate. 15 μg of each sample was loaded into each of two pH 3-10 isoelectric focusing strips (Amersham BioSciences) and separated to equilibrium. The strips were then rinsed and loaded onto 10.5% (37 kD and 39 kD) or 8.5% (73 kD) polyacrylamide gels (Amersham BioSciences) for second dimension electrophoresis. After electrophoresis, fluorescence images of the gels were acquired and verified for consistency using Image Quant software (version 6.0, Amersham BioSciences). One of the gels was transferred electrophoretically to a 0.2 μm pore nitrocellulose membrane (Whatman). A Western blot was performed on the transferred membrane using maternal plasma samples which are positive for the antigen sample used on the blot and a chemiluminescent image of the resulting blot was acquired using on a Fluor Chem 8900 imager (Alpha Innotech). The image size was adjusted using internal markers to match identically with the other, non-transferred 2-D gel for spot picking alignment. The spots identified on the Western blot image were picked from the 2 D gel using an Ettan Spot Picker (Amersham BioSciences).

Mass Spectrometry

Spots identified by Western blot and mapped back and picked from the duplicate 2-D gel and were washed and digested with Trypsin (Promega). The tryptic peptides were desalted using a Zip-tip C18 (Millipore), eluted from the Zip-tip and spotted on the MALDI plate (model ABI 01-192-6-AB). MALDI-TOF MS and TOF/TOF tandem MS/MS were performed on an ABI 4700 mass spectrometer (Applied Biosystems, Framingham, Mass.). MALDI-TOF mass spectra and TOF/TOF tandem MS fragmentation spectra were acquired for each sample, averaging 4000 laser shots per fragmentation spectrum on each of the 10 most abundant ions present in each sample. Both the resulting peptide mass and the associated fragmentation spectra were analyzed by a GPS Explorer workstation equipped with MASCOT search engine (Matrix science) and used to query the database of National Center for Biotechnology Information non-redundant (NCBInr). Searches were performed without constraining protein molecular weight or isoelectric point, with variable carbamidomethylation of cysteine and oxidation of methionine residues, and with one missed cleavage also allowed in the search parameters. Candidates with either protein score C.I. % or Ion C.I. % greater than 95 were considered significant.

Antigen Verification

Western Blots

Purified native LDH (Cell Sciences, Canton, Mass.), recombinant full length CYP (Abnova, Taipei, Taiwan), recombinant full length YBX1 (Abnova), recombinant full length CRMP1 (OriGene, Rockville, Md.) and recombinant full length STIP1 (Abnova) human proteins were tested individually by Western blot using maternal plasma with reactivity to RFB protein as the primary antibody. Commercially available polyclonal antibodies for LDH (Abcam, Cambridge, Mass.), CYP (Sigma), YBX1 (Abcam), CRMP1 (Abcam) and STIP1 (Abcam) were used as positive controls.

Blocking Studies

Figure 4:
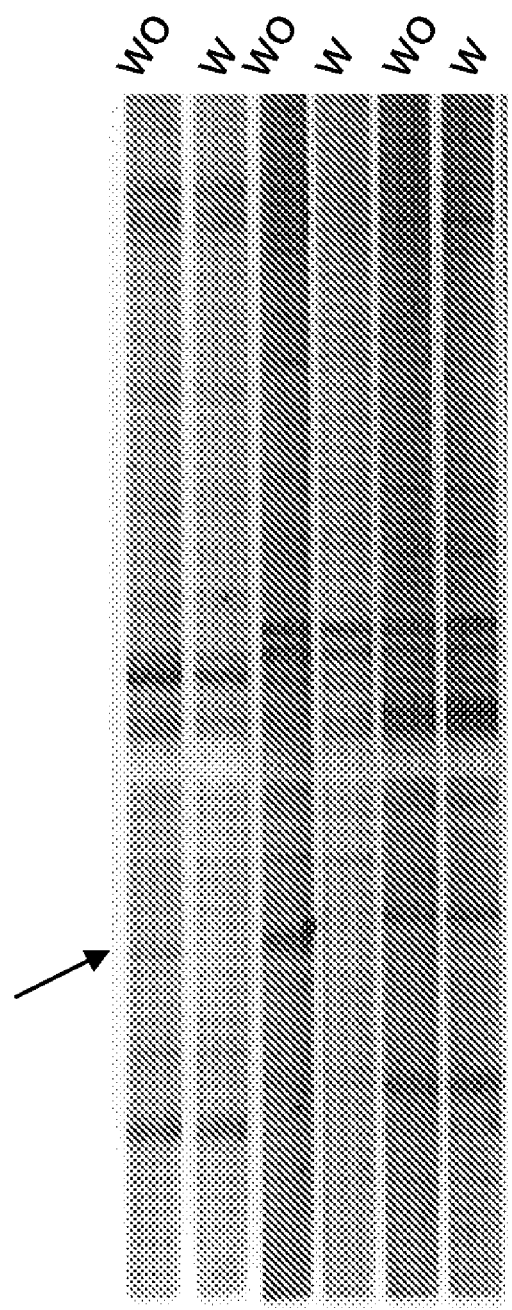
FIG. 4 illustrates a representative Western blot using purified from human erythrocytes containing LDHA and B. The LDH that used for Western blot and ELISA was purified from human erythrocytes and contains both the A and B subunits. Western blots with recombinant pure LDHA or LDHB demonstrated that mothers can display IgG reactivity to either or both subunits.
Figure 5:
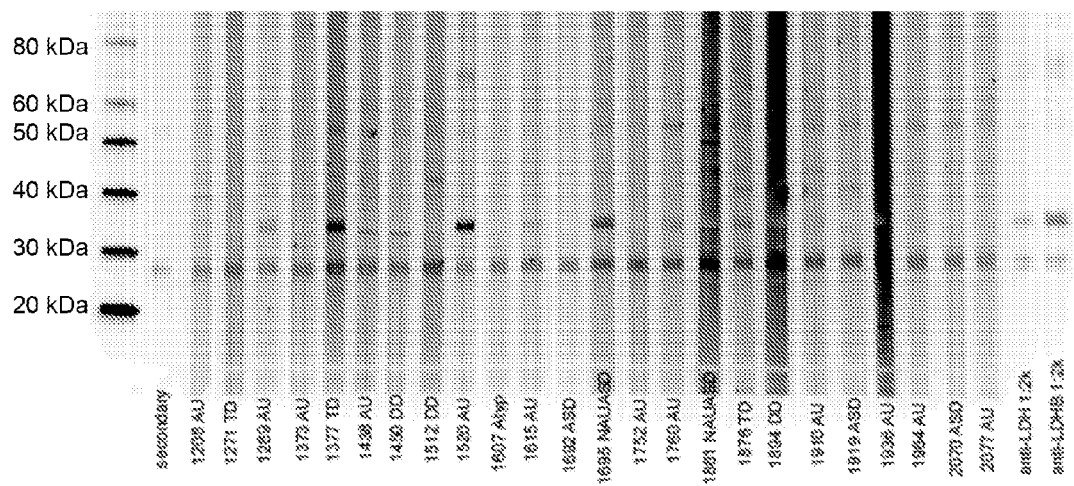
FIG. 5 illustrates a representative Western blot using purified from human erythrocytes containing LDHA and B. The LDH that used for Western blot and ELISA was purified from human erythrocytes and contains both the A and B subunits, which share 90% sequence homology. Western blots with recombinant pure LDHA or LDHB demonstrated that mothers can display IgG reactivity to either or both subunits. Approximately 30% of mothers of children with autism are positive for antibodies that bind to either or both LDHA and LDHB. Among positive mothers, all reacted to both A and B subunits.
Figure 6:
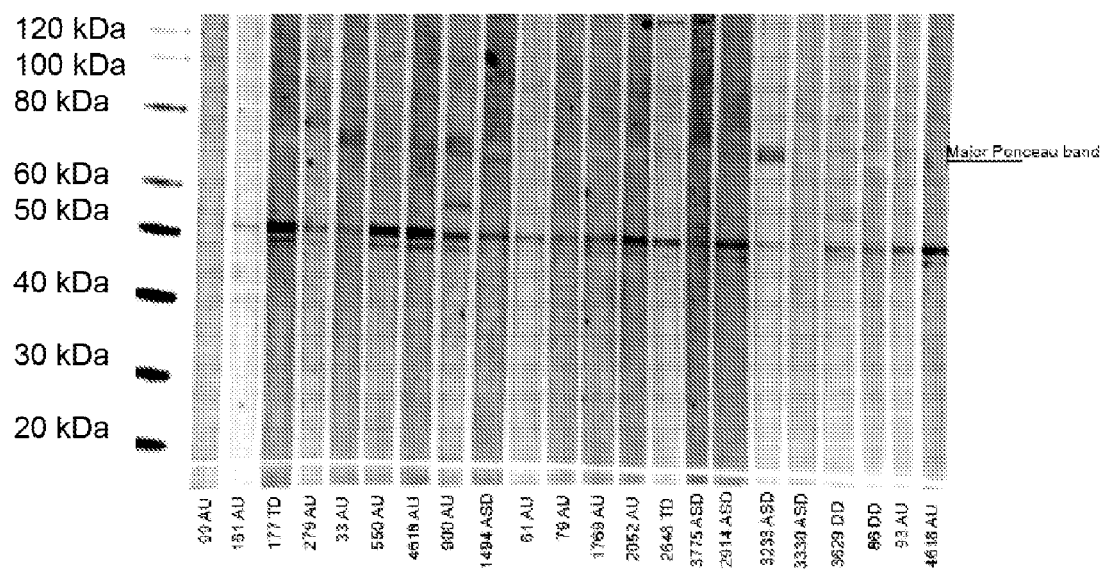
FIG. 6 illustrates a representative Western blot of positive and negative subjects who displayed reactivity to a band at 39 kDa by blot of fetal monkey brain. There are two proteins that appear to be associated with ASD that were identified by bands at approximately 39 kDa. These were guanine deaminase ("GDA") and Y box binding protein 1 (YBX1). Those individuals positive to GDA all had bands at 39 kDa. However, not all 39 kDa positive individuals were GDA positive. Approximately 26% of mothers of children with autism are positive for IgG targeting GDA.
Figure 7:
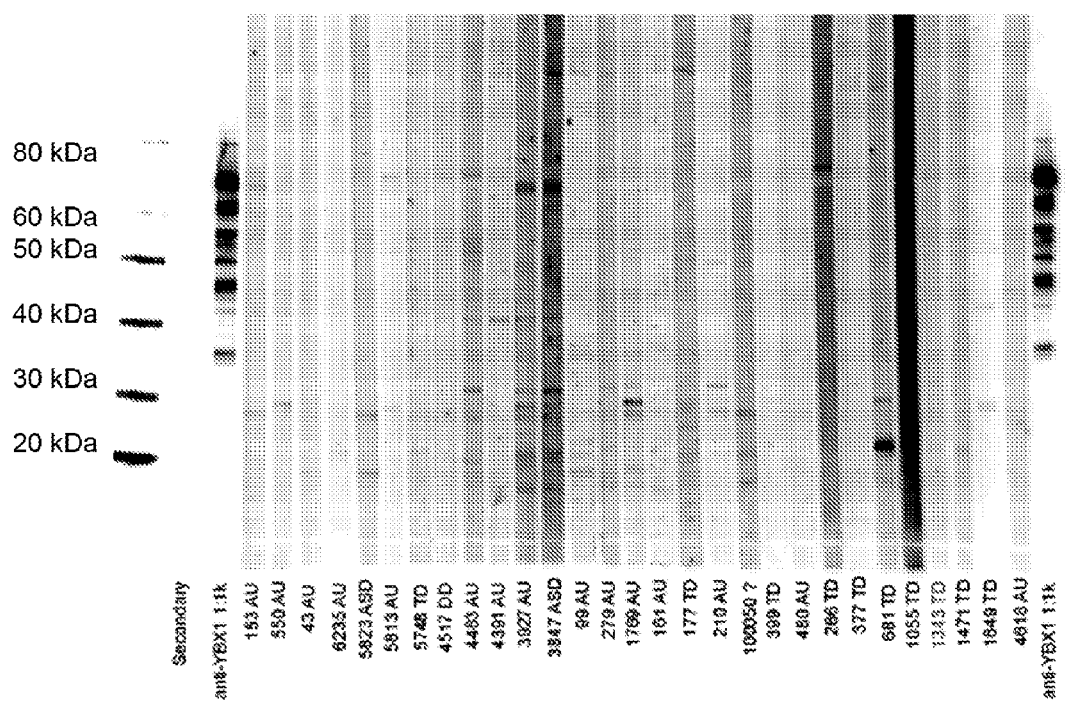
FIG. 7 illustrates a representative Western blot of positive and negative subjects who displayed reactivity to a band at 39 kDa by blot of fetal monkey brain. Those individuals positive to YBX1 all had bands at 39 kDa. However, not all 39 kDa positive individuals were YBX1 positive. Approximately 11% of mothers of children with autism are positive for YBX1. Other proteins having an apparent molecular weight of 39 kDa and bound by maternal antibodies include Eukaryotic Translation and Elongation Factor 1A1 ("EEF1A1") and Microtubule-associated protein Tau ("MAPT").
Figure 8:
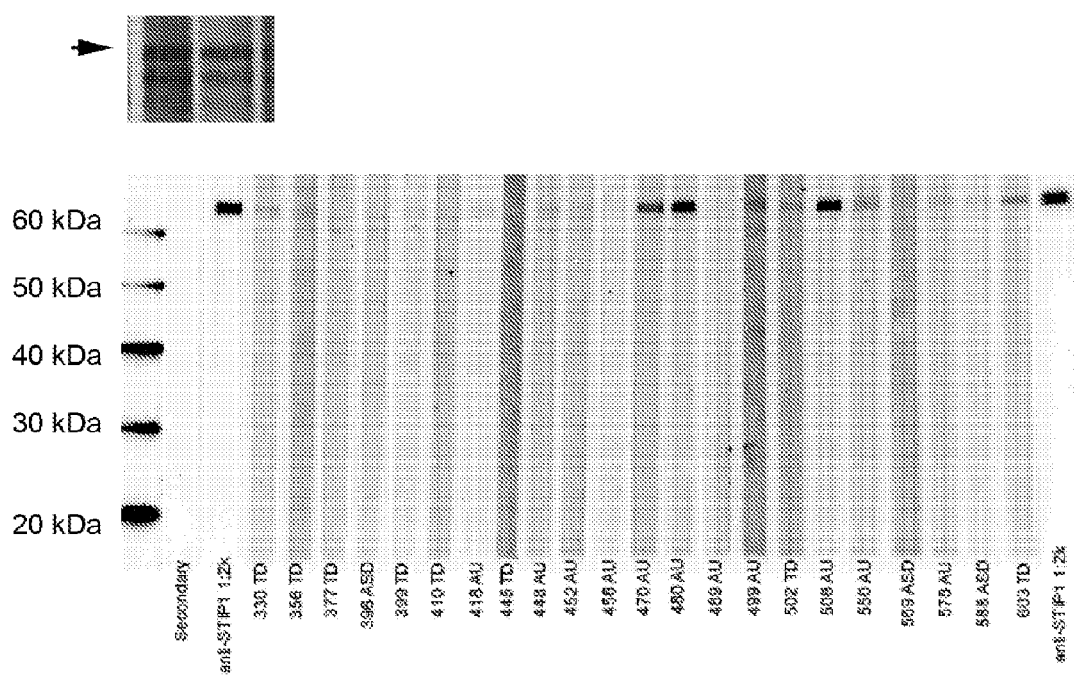
FIG. 8 illustrates a representative Western blot of positive and negative subjects who displayed reactivity to a band at 73 kDa by blot of fetal monkey brain. There are 2 bands within the region of 73 kDa often seen by Western blot analysis of fetal monkey brain when stained with maternal antibodies. The bands form a very tight doublet as seen in the inset. The upper band of this doublet has been determined to be Stress Induced Phosphoprotein 1 ("STIP1"). The lower band was determined to be Collapsin Response Mediator Protein 1 ("CRMP1"). A positive anti-STIP1 antibody from a commercial source shows bands at an apparent MW of 63 kDa. Approximately 32% of mothers of children with autism are positive for antibodies against CRMP1 and approximately 59% of the mothers of children with autism are positive for antibodies against STIP1.
Figure 9:
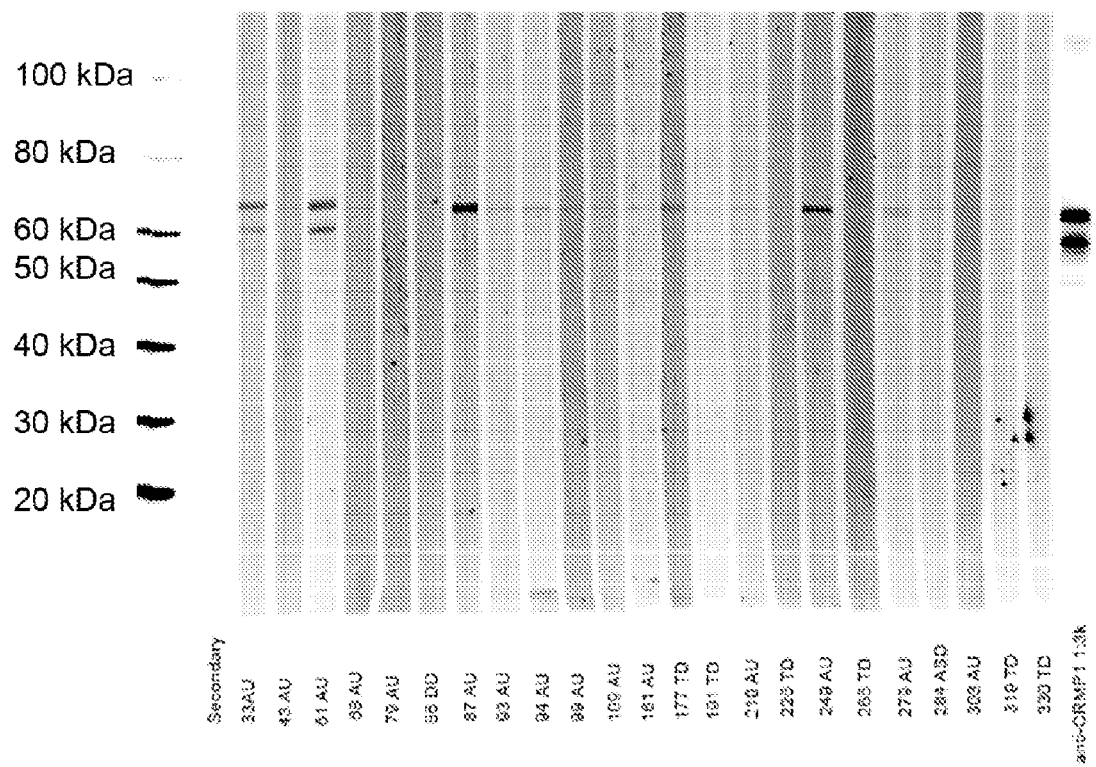
FIG. 9 illustrates a representative Western blot of positive and negative subjects who displayed reactivity to a band at 73 kDa by blot of fetal monkey brain. Positive anti-CRMP1 antibody from a commercial source shows bands at an apparent MW of 60 kDa and 63 kDa. Other proteins having an apparent molecular weight of 73 kDa and bound by maternal antibodies include Dihydropyrimidinase-like Protein 2 ("DPYSL2"), Dynamin 1-like protein ("DNM1L"), neurofilament, light polypeptide ("NEFL") and Radixin ("RDX").
Figure 10:
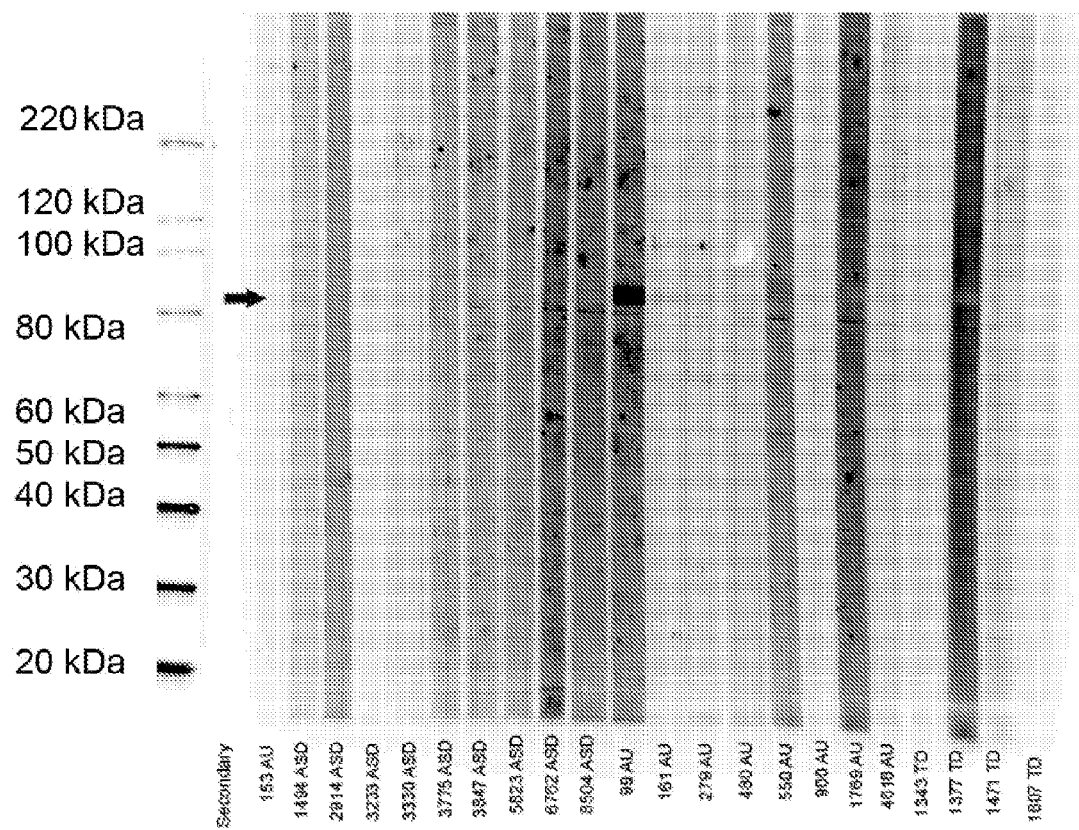
FIG. 10 illustrates a representative Western blot of DPYSL2. This band is found in only a few individuals.
Figure 11:
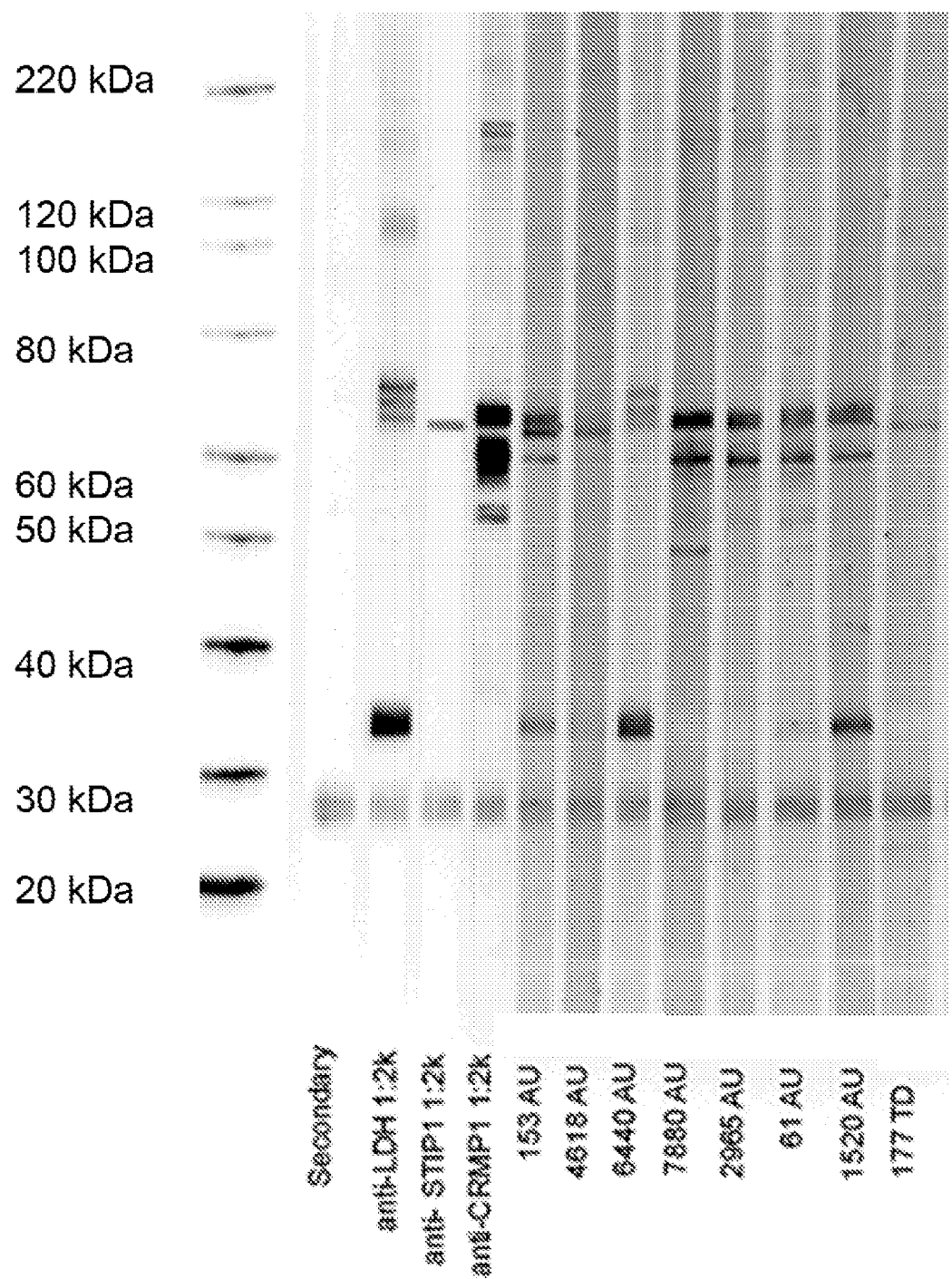
FIG. 11 illustrates a representative combined Western blot containing pure LDH, STIP1 and CRMP1. Purified forms of the target proteins were run together as a substrate for Western blot and probed with various samples. Lane one is a secondary antibody only control and the band across the bottom of each strip is residual human IgG that is present in the LDH preparation. Lanes 2-4 are probed with positive control commercial antisera to the respective proteins. Lane 5 (AU 153) is the positive plasma control that was used to identify the target proteins. This individual has reactivity for all 3 antigens both the original western blot of crude fetal monkey brain (FMB), and with the more purified versions. Individual 4618 AU is faintly positive for the 37 kDa band by FMB, and primarily binds to proteins with apparent molecular weights of 37 kDa and 73 kDa. Subject 4618 is also positive for GDA (the 39 kDa band). Various other band configurations are illustrated here as well.

Maternal plasma samples which showed reactivity to LDH, as well as control plasma samples, were diluted 1:400 and incubated for 20 hrs at 4° C. in buffer alone or buffer containing 100 ug of purified LDH. These samples were then used to probe Western blot strips containing RFB (FIG. 4). Among mothers positive for LDH reactivity, band intensity was substantially reduced among the samples pre-incubated with LDH protein. Pre-incubation with LDH did not affect maternal plasma reactivity to other antigens.

ELISA

Purified human erythrocyte-derived LDH was diluted in carbonate coating buffer and a total of 2 μg LDH was added to each well of a 96-well plate and incubated 16 hrs at 4° C. The plate was then rinsed and blocked with 5% bovine serum albumin and incubated with maternal plasma diluted 1:600 for 1 hr at room temperature. Plates were then washed and incubated with horseradish peroxidase conjugated goat anti-human IgG (Invitrogen) diluted 1:25000 for 1 hr. Plates were then washed, incubated with Ultra TMB-ELISA substrate (Thermo Scientific) and read at 450 nm.

LDH Enzyme Inhibition

Decrease in absorbance at 340 nm in a BioSpec 1600 spectrophotometer (Shimadzu) was used to monitor the effect of maternal antibodies on LDH enzyme function. 40 μg of purified maternal IgG antibodies, from mothers with LDH reactivity as well as controls, were incubated for 30 minutes at room temperature with 1.5 μg of purified human LDH. The antibody/enzyme mixtures were added to a cuvette containing 100 μl of 6.6 mM reduced Nicotinamide Adenine Dinucleotide (Sigma) and 100 μl of 30 mM Sodium Pyruvate (Sigma) diluted in 2.8 ml of 0.125 M Tris-HCl pH 8.0 in a 3 ml Acryl-Cuvette (Sarstedt). A cuvette containing Tris-HCl was used as blank. Absorbance change over 2 minutes was recorded for each sample.

Results

Antigen Identification

Figure 2:
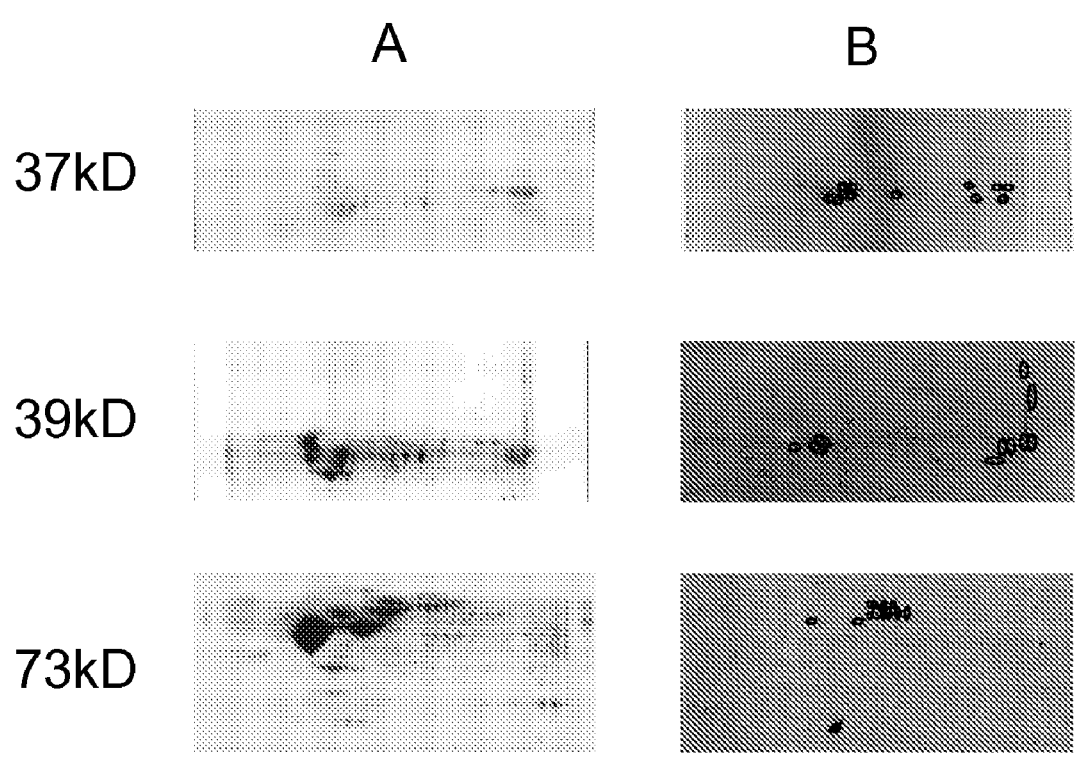
FIG. 2 illustrates 2-D gel and Western blot images. Rhesus fetal brain (RFB) protein fractions of containing targets of maternal antibodies were fluorescently labeled and separated on 2-D gels. A) Fluorescence image of labeled 37 kD, 39 kD or 73 kD proteins after 2-D separation. B) Chemiluminescent image of 2-D Western blot probed with diluted plasma from mothers reactive against each of the antigens. Circles represent spots of reactivity between maternal antibodies and cognate antigens on the 2-D blot which were used to guide spot picking from a duplicate 2-D gel.

Separate 2-D Western blot were performed for Prep cell fractions containing the 37 kDa, 39 kDa or 73 kDa antigens (FIG. 2). Each blot was probed with 1:400 diluted maternal plasma from a randomly selected AUM who displays reactivity to the corresponding band. Multiple spots were observed on each 2-D Western blot, and all clearly defined spots were selected for mass spectrometry. Analysis of mass spectrometric data yielded proteins for each spot and those with a 100% CI were selected for verification (Table 1).

TABLE 1

Mass Spectrometry Results

| Spot Number | Protein | Accession # | Protein MW (Daltons) | Protein Score % CI |
|---|---|---|---|---|
| 1 | Lactate Dehydrogenase A | gi\|109107092 | 39754.9 | 100 |
| 2 | Lactate Dehydrogenase B | gi\|109095927 | 35575.6 | 100 |
| 3 | Cypin | gi\|55957350 | 44161.1 | 100 |
| 4 | Y Box Binding Protein 1 | gi\|54040031 | 35924.1 | 100 |
| 5 | Stress-Induced Phosphoprotein 1 | gi\|73909112 | 68003.2 | 100 |
| 6 | Collapsin Response Mediator Protein 1 | gi\|4503051 | 62144.7 | 100 |
| 7 | Dihydropyrimidinase-like Protein 2 | gi\|62087970 | 68183.7 | 100 |

Antigen Verification

Lactate Dehydrogenase

Figure 3:
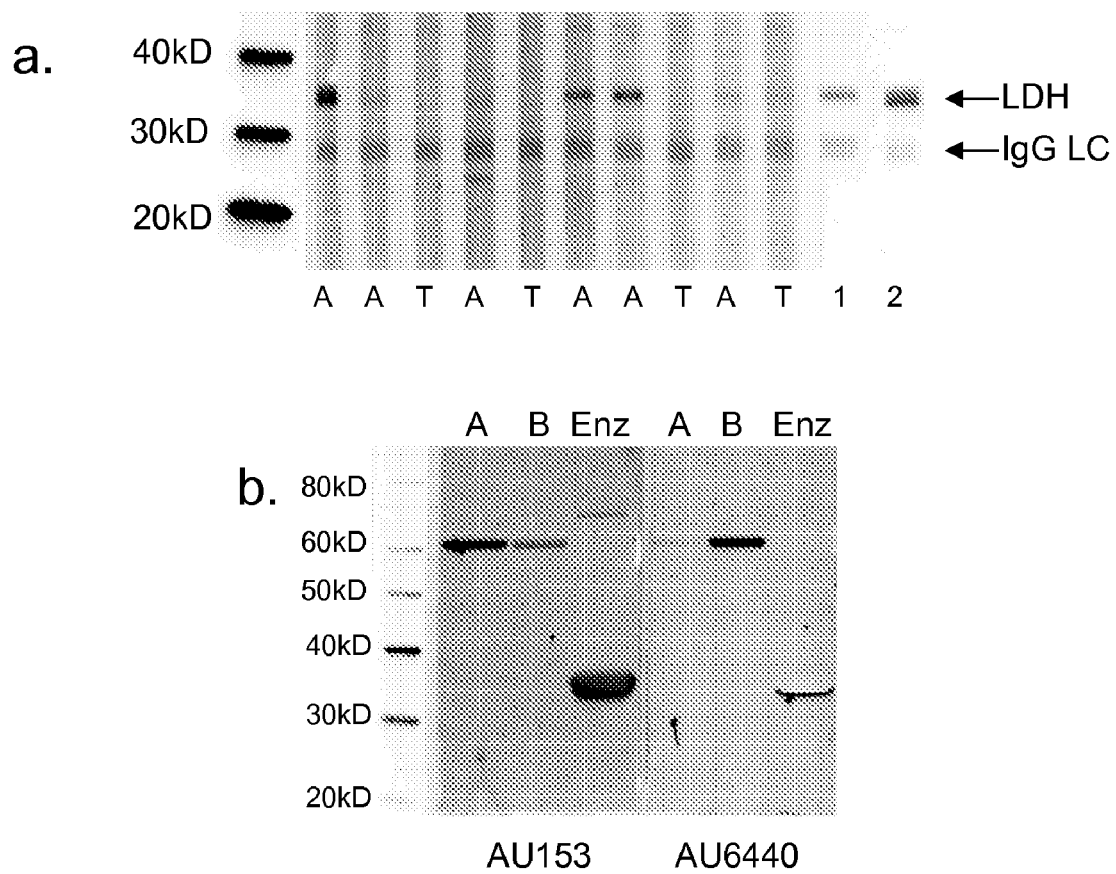
FIG. 3 illustrates a Western blot of recombinant or purified LDH. a) Representative Western blot of purified human LDH probed with 1:400 diluted maternal plasma from AUM (A) or TDM (T). Strip 1 is probed with 1:2000 diluted goat anti-human LDH and strip 2 is probed with 1:2000 diluted rabbit anti-human LDHB. b) Western blot of recombinant human GST-tagged LDHA (A), recombinant human GST-tagged LDHB (B) or purified native human LDH (Enz) was probed with 1:400 diluted maternal plasma, demonstrating variable reactivity to LDH subunits.

Native purified LDH and full-length recombinant LDHA and LDHB subunits were used for verification of maternal IgG reactivity by Western blot (FIG. 3). LDHA and LDHB subunits share approximately 90% sequence homology and although some variation was observed in reactivity to the A and B subunits, all maternal antibodies which were reactive to LDH recognized both subunits. Screening of all maternal plasma samples was thus carried out with purified LDH which contains both subunits.

Discussion

Abnormalities in the maternal immune milieu during pregnancy have been implicated in AU in several studies. Prominent among them are reports of maternal antibodies which react against fetal proteins. Facilitated passage of IgG antibodies is a well established phenomenon thought to generally provide protection for the newborn child (Garty, et al., *Clin Diagn Lab Immunol*, (1994) 1(6): 667-9); and such antibodies are known to persist for up to six months post-natal (Heininger, et al., *Vaccine*, (2006) 24(16):3258-60). However, together with IgG antibodies that are immunoprotective, autoantibodies that react to fetal 'self'-proteins can also cross the placenta. A recent report demonstrated maternal IgG antibody reactivity to rodent Purkinje cells in a mother of multiple children with ASD, as well as the presence of behavioral deficits in pups of a mouse injected during gestation with her serum (Dalton, et al., *Ann Neurol*, (2003) 53(4):533-7). In another study, mothers of children with autism and their affected children were found to have consistent patterns of antibody reactivity against rat pre-natal (day 18) brain proteins. In contrast, unaffected children and control mothers had alternative patterns of reactivity (Zimmerman, et al., *Brain Behav Immun*, (2007) 21(3):351-7).

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, patent applications and sequence accession numbers cited herein are hereby incorporated by reference in their entirety for all purposes.

What is claimed is:

1. A method of determining a risk of a human offspring for developing an autism spectrum disorder (ASD) comprising detecting in a biological sample from the mother or potential mother of the offspring the presence of maternal antibodies that bind to one or more biomarkers selected from the group consisting of a lactate dehydrogenase (LDH) protein, a guanine deaminase (GDA) protein, a collapsin response mediator protein 1 (CRMP1) protein, a dihydropyrimidinase-like protein 2 (DPYSL2) protein, a stress-induced phosphoprotein 1 (STIP1) protein and a Y Box Binding Protein 1 (YBX1) protein, wherein said biological sample is selected from the group consisting of blood, serum, plasma, and saliva, and wherein the presence of maternal antibodies that bind to the one or more biomarkers indicates an increased risk of the offspring for developing an ASD.

2. The method of claim 1, wherein the biological sample is selected from the group consisting of blood, serum, and plasma.

3. The method of claim 1, wherein the presence of maternal antibodies that bind to one or more biomarkers selected from the group consisting of an LDH protein, a GDA protein, a CRMP1 protein and an STIP1 protein are detected.

4. The method of claim 1, wherein the presence of maternal antibodies that bind to one or more biomarkers selected from the group consisting of an LDH protein, a CRMP1 protein and an STIP1 protein are detected.

5. The method of claim 1, wherein the offspring is a neonate.

6. The method of claim 1, wherein the offspring is a fetus.

7. The method of claim 1, wherein said biological sample is obtained prior to conception and said detecting occurs prior to conception.

8. The method of claim 1, wherein the mother or potential mother has a child with an ASD.

9. The method of claim 1, wherein the mother or potential mother has a familial history of ASD or autoimmune disease.

10. The method of claim 1, comprising detecting in the biological sample the presence of maternal antibodies that bind to the DPYSL2 protein.

11. The method of claim 1, wherein the LDH protein is an LDH-A subunit and/or an LDH-B subunit.

12. The method of claim 1, comprising detecting in the biological sample the presence of maternal antibodies that bind to the GDA protein.

13. The method of claim 1, wherein the method comprises contacting the sample with one or more synthetic or recombinant polypeptides selected from the group consisting of a synthetic or recombinant polypeptide comprising an amino acid sequence of a lactate dehydrogenase (LDH), a guanine deaminase (GDA), a collapsin response mediator protein 1 (CRMP1), a stress-induced phosphoprotein 1 (STIP1), and a Y Box Binding Protein 1 (YBX1).

14. The method of claim 13, wherein the one or more synthetic or recombinant polypeptides are attached to a solid support.

15. The method of claim 13, wherein the maternal antibodies are detected by Western blot, dot blot, ELISA, radioimmunoassay, immunoprecipitation, electrochemiluminescence, immunofluorescence, or multiplex bead assay.

16. The method of claim 13, wherein the maternal antibodies are detected by a detectable signal selected from the group consisting of fluorescence, chemiluminesence, color, and radioactivity.

17. The method of claim 13, wherein the maternal antibodies are detected by FACS analysis, scintillation proximity assay (SPA), FRET, or sandwich-type antibody assay.

18. The method of claim 10, further comprising detecting in the biological sample the presence of maternal antibodies that bind to the YBX1 protein.

19. The method of claim 1, wherein the presence of maternal antibodies that bind to one or more biomarkers selected from the group consisting of an LDH protein, a GDA protein and an STIP1 protein are detected.

20. The method of claim 1, wherein the presence of maternal antibodies that bind to one or more biomarkers selected from the group consisting of a GDA protein, a CRMP1 protein and an STIP1 protein are detected.

* * * * *

SEQUENCE LISTING

<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: synthetic HLA class II gene promoter Y-box

<400> SEQUENCE: 1
ctgattggcc aa                                                          12

<210> SEQ ID NO 2
<211> LENGTH: 200
<212> TYPE: PRT
<213> ORGANISM: Artificial Sequence
<220> FEATURE:
<223> OTHER INFORMATION: Description of Artificial Sequence:poly Gly
      flexible linker
<220> FEATURE:
<221> NAME/KEY: VARIANT
<222> LOCATION: (6)...(200)
<223> OTHER INFORMATION: Xaa = Gly or absent

<400> SEQUENCE: 2

Gly Gly Gly Gly Gly Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
           100                 105                 110

Xaa Xaa Xaa Xaa Xaa Xaa Xaa Xaa Xaa Xaa Xaa Xaa Xaa Xaa Xaa
       115                 120                 125

Xaa Xaa Xaa Xaa Xaa Xaa Xaa Xaa Xaa Xaa Xaa Xaa Xaa Xaa Xaa
   130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa
        195                 200